United States Patent
Watts et al.

(10) Patent No.: US 10,512,938 B2
(45) Date of Patent: Dec. 24, 2019

(54) ROTARY SEPARATION APPARATUS AND PROCESS

(71) Applicant: The Original Resinator, LLC, Graton, CA (US)

(72) Inventors: James Eugene Watts, Willits, CA (US); Travis Jeremy Arnovick, Graton, CA (US)

(73) Assignee: The Original Resinator LLC, Graton, CA (US)

( * ) Notice: Subject to any disclaimer, the term of this patent is extended or adjusted under 35 U.S.C. 154(b) by 0 days.

(21) Appl. No.: 15/832,614

(22) Filed: Dec. 5, 2017

(65) Prior Publication Data
US 2019/0083558 A1    Mar. 21, 2019

Related U.S. Application Data

(63) Continuation-in-part of application No. 15/641,254, filed on Jul. 4, 2017.
(Continued)

(51) Int. Cl.
*B07B 1/22* (2006.01)
*B01D 11/02* (2006.01)
(Continued)

(52) U.S. Cl.
CPC .................. *B07B 1/22* (2013.01);
*A23L 3/36* (2013.01); *A23L 3/361* (2013.01);
*A23L 3/37* (2013.01); *A23L 3/375* (2013.01);
*A23L 3/44* (2013.01); *B01D 11/02* (2013.01);
*B01D 11/0226* (2013.01); *B01D 11/0246* (2013.01); *B01D 11/0273* (2013.01); *B01D 45/16* (2013.01); *B01D 46/26* (2013.01);
*B01D 46/30* (2013.01); *B01D 50/002* (2013.01); *B07B 7/06* (2013.01); *B07B 9/00* (2013.01); *F25D 3/11* (2013.01);
(Continued)

(58) Field of Classification Search
CPC .... B01D 2273/28; B01D 39/04; B01D 45/16; B01D 46/26; B01D 46/30; B01D 50/002; B01D 11/0273; B04C 5/10; B07B 7/06; B07B 9/00; B07B 1/22; F26B 25/005; Y10S 55/03; A61K 2236/30
See application file for complete search history.

(56) References Cited

U.S. PATENT DOCUMENTS 3,079,761 A    3/1963 Toulmin, Jr.
4,051,771 A    10/1977 Miyata et al.
(Continued)

FOREIGN PATENT DOCUMENTS

WO    200400919 A2    1/2014

OTHER PUBLICATIONS

"Home-made hash", by Wombat, dated Mar. 8, 2005, downloaded from <http://www.poUv/video/2005/03/08/4117/>.
(Continued)

*Primary Examiner* — John Kim
(74) *Attorney, Agent, or Firm* — Edward S. Sherman

(57) ABSTRACT

A rotary separation apparatus is deployed in a process for separating resinous trichomes rich in flavoring, aromatic and/or medicinal components produced in plant trichome glands from unwanted plant matter. A liquid freezing agent is introduced into a container of the plant matter to fragment the undesirable matter while the desired portion rich in trichome remain intact.

28 Claims, 16 Drawing Sheets

Related U.S. Application Data

(60) Provisional application No. 62/358,988, filed on Jul. 6, 2016.

(51) Int. Cl.

| | | |
|---|---|---|
| *B07B 9/00* | (2006.01) | |
| *B07B 1/18* | (2006.01) | |
| *B01D 46/26* | (2006.01) | |
| *A23L 3/44* | (2006.01) | |
| *A23L 3/375* | (2006.01) | |
| *B07B 7/06* | (2006.01) | |
| *B01D 50/00* | (2006.01) | |
| *B01D 46/30* | (2006.01) | |
| *B01D 45/16* | (2006.01) | |
| *A23L 3/37* | (2006.01) | |
| *A23L 3/36* | (2006.01) | |
| *F25D 3/11* | (2006.01) | |
| *F26B 25/00* | (2006.01) | |

(52) U.S. Cl.
CPC ...... *A61K 2236/30* (2013.01); *B01D 2273/28* (2013.01); *F26B 25/005* (2013.01)

(56) References Cited

U.S. PATENT DOCUMENTS

| | | |
|---|---|---|
| 4,137,723 A | 2/1979 | Tyree, Jr. |
| 4,157,061 A | 6/1979 | Margus, Jr. |
| D280,628 S | 9/1985 | Besson |
| 4,795,651 A | 1/1989 | Johnson et al. |
| 5,964,100 A | 10/1999 | Wisniewski |
| 6,158,591 A | 12/2000 | Delp |
| 7,008,528 B2 | 3/2006 | Mitchell et al. |
| 8,640,877 B1 | 2/2014 | Pastorius |
| 8,955,687 B1 | 2/2015 | Dews et al. |
| 9,066,910 B2 | 6/2015 | Rosenblatt et al. |
| 2004/0206686 A1* | 10/2004 | Reinach .............. B04B 3/02 210/360.1 |
| 2009/0250383 A1 | 10/2009 | Young et al. |
| 2004/0271940 | 9/2014 | Wurzer |
| 2014/0271940 A1 | 9/2014 | Wurzer |

OTHER PUBLICATIONS

"Inside the Trichome", by Bubbleman and Jeremiah Vandermeer, published on Cannabis Culture on Jun. 12, 2009.

PCT Search report in PCT/US2018/064036, dated Mar. 7, 2019.

Youtube video at URL::https://www.youtube.com/watch?v=BQuxTFugMoc, currently dated Sep. 1, 2015 at the URL The attachment includes what are believed to be the most material still images from this video sequence.

Youtube video at URL:: https://www.youtube.com/watch?v=1zJiVnVdxdM, currently dated Sep. 16, 2016 The attachment includes what are believed to be the most material still images from this video sequence.

https://www.youtube.com/watch?v=Gb03Xm4yRLO, currently dated at this URL as Jun. 2, 2016 The attachment includes what are believed to be the most material still images from this video sequence.

Webpage from www.pollinator.nl, retrieved prior to Jul. 6, 2016.

\* cited by examiner

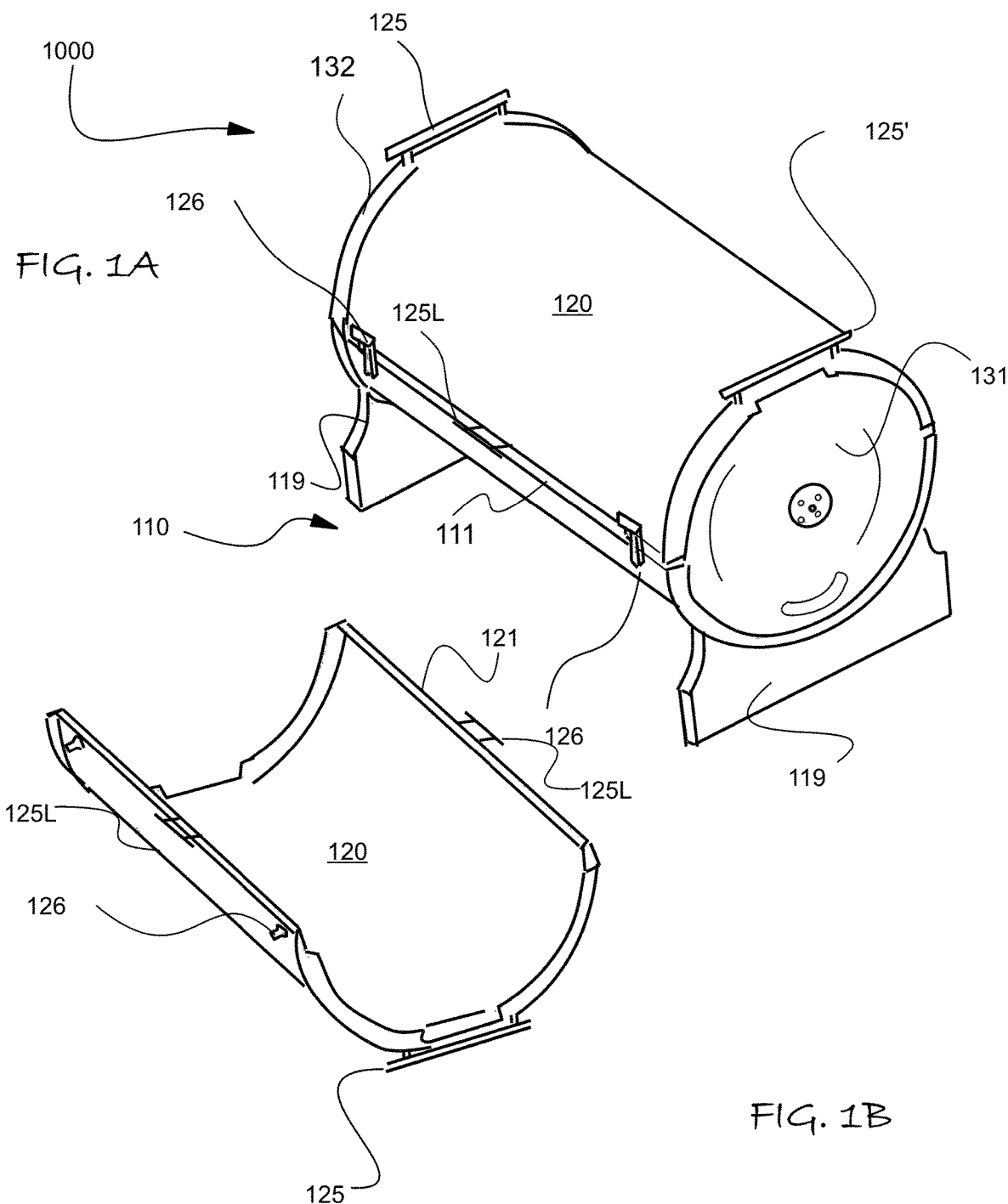

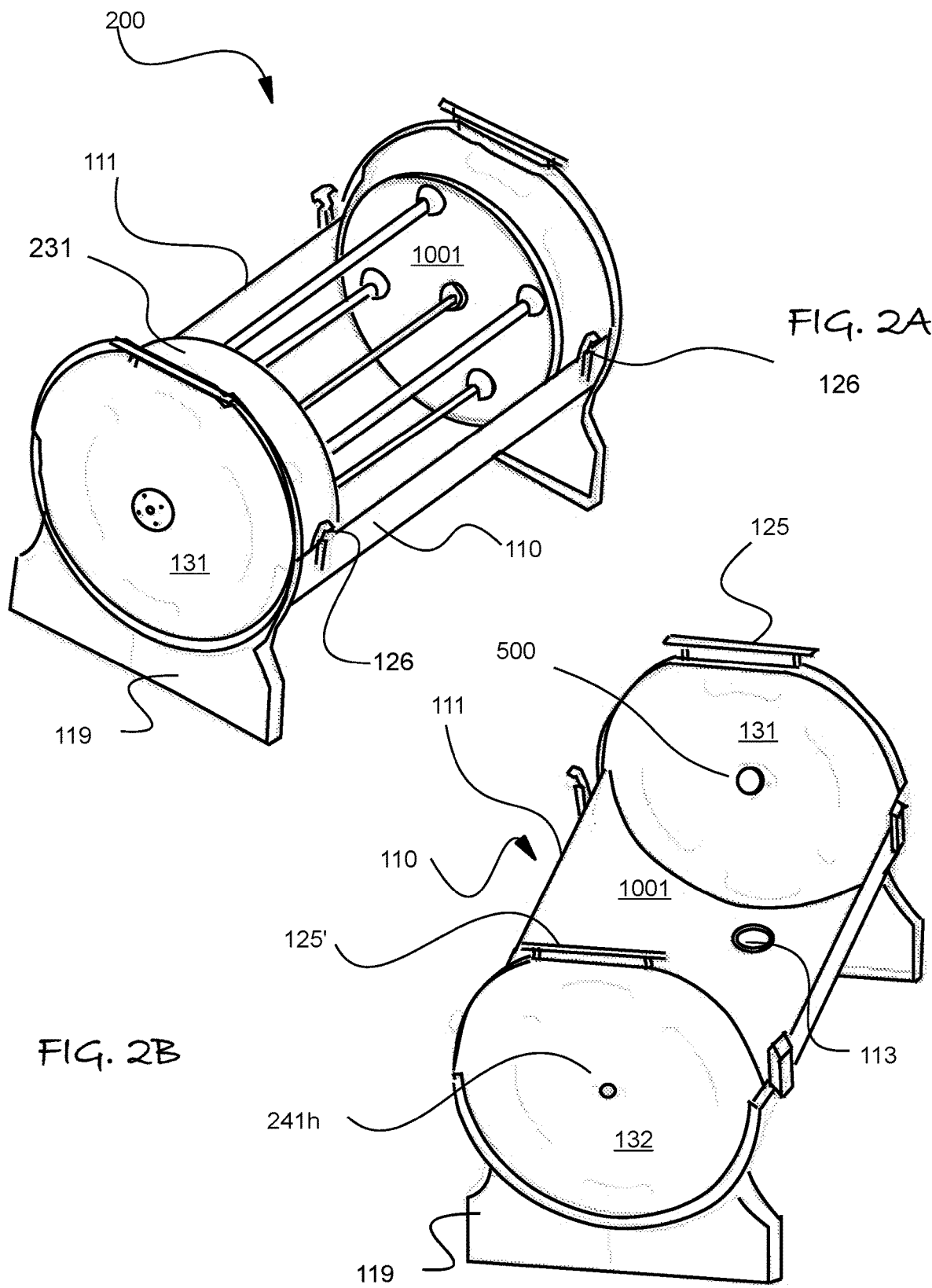

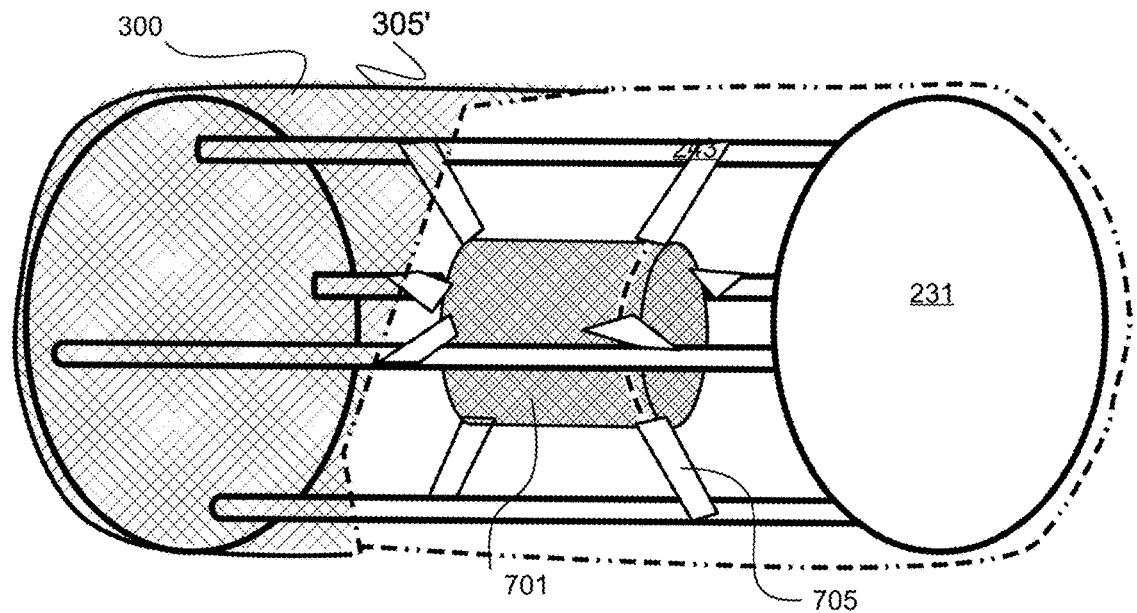
FIG. 10B
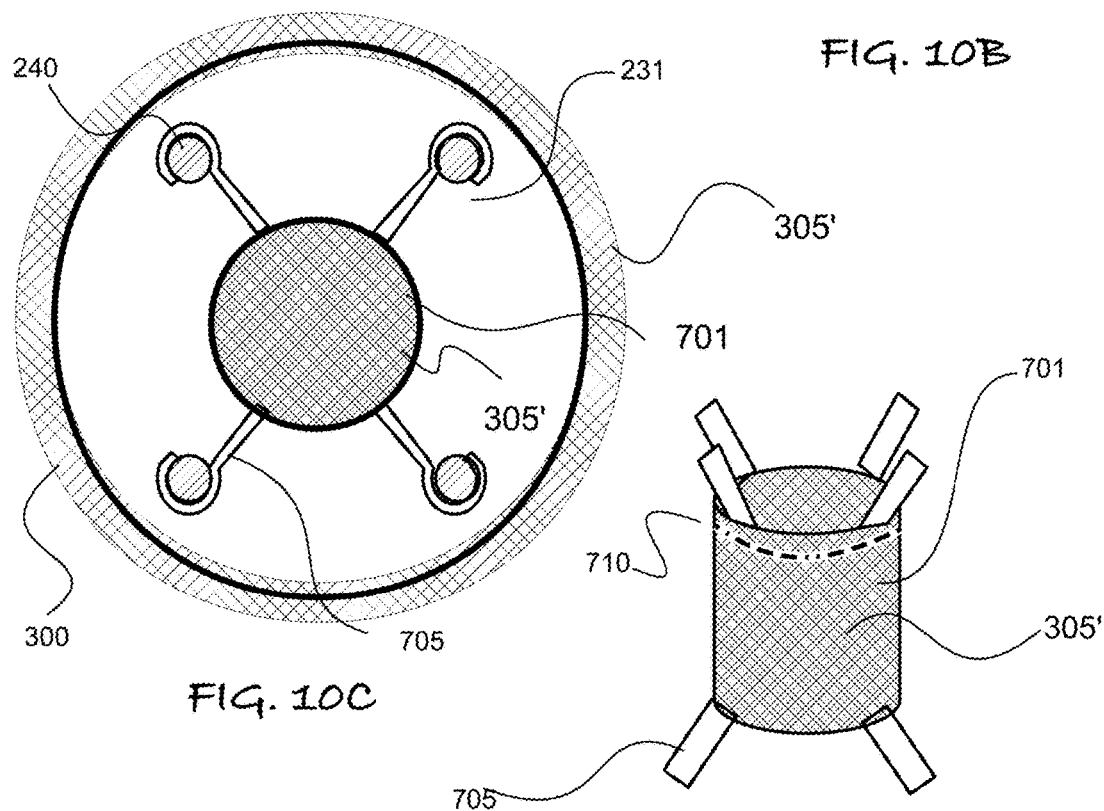
FIG. 10C
FIG. 10A

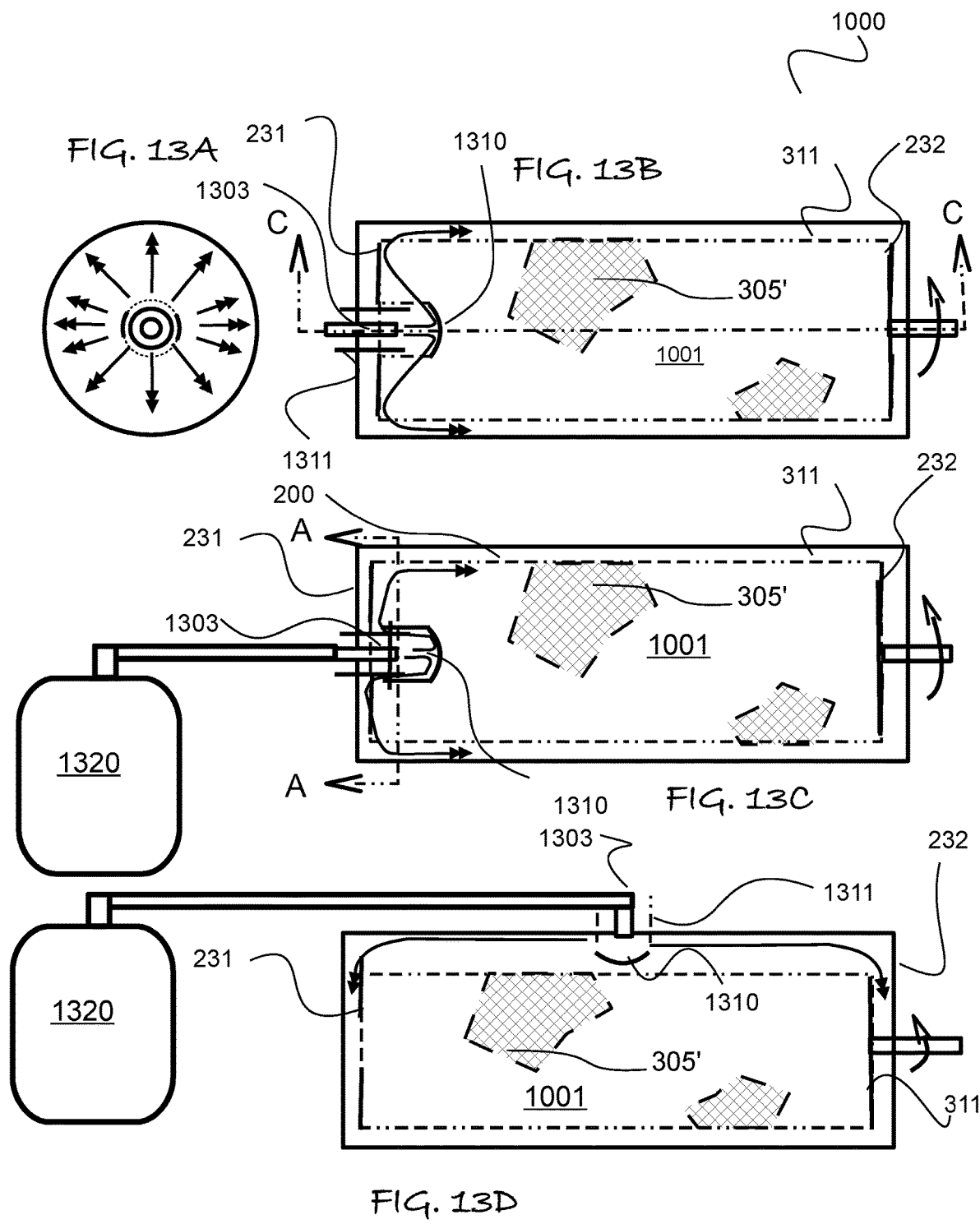

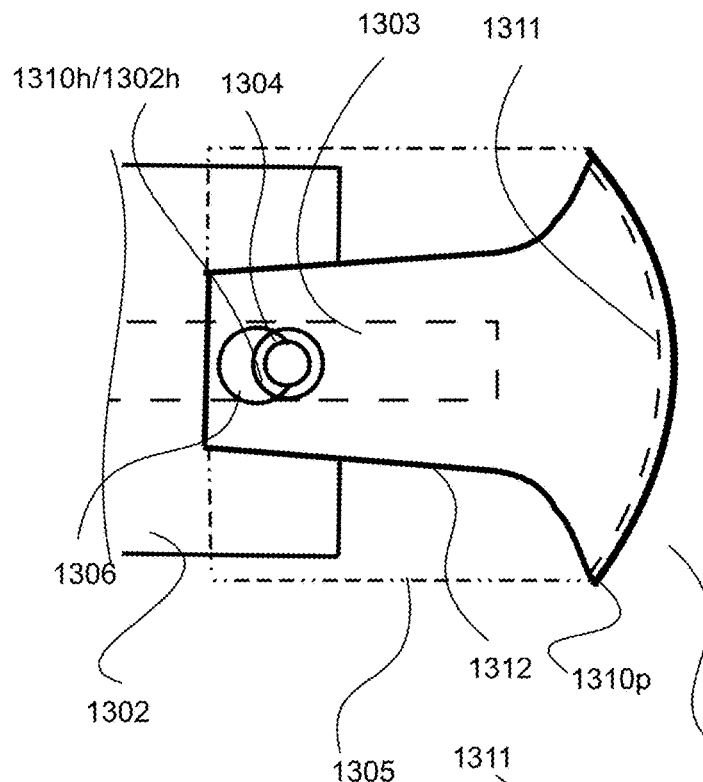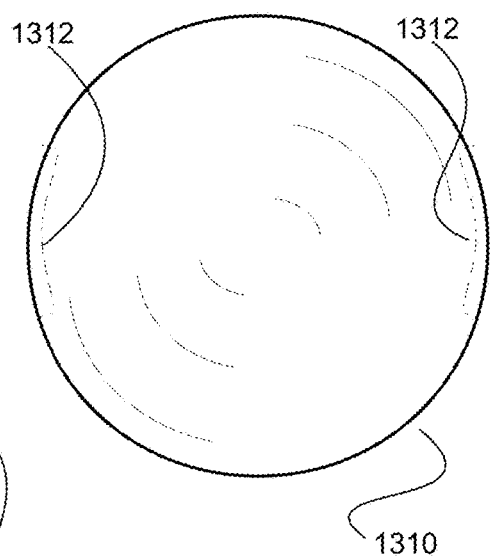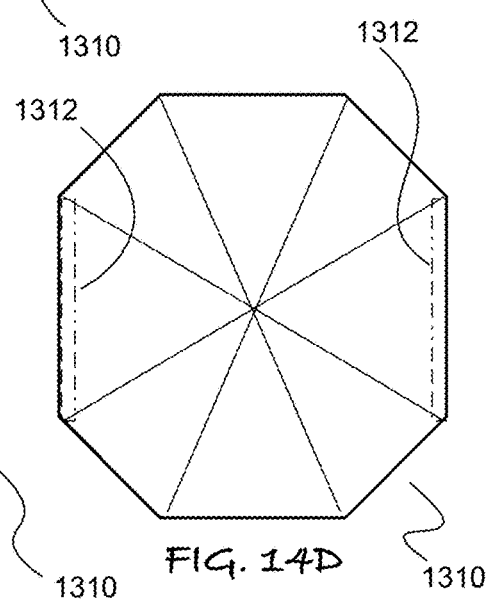

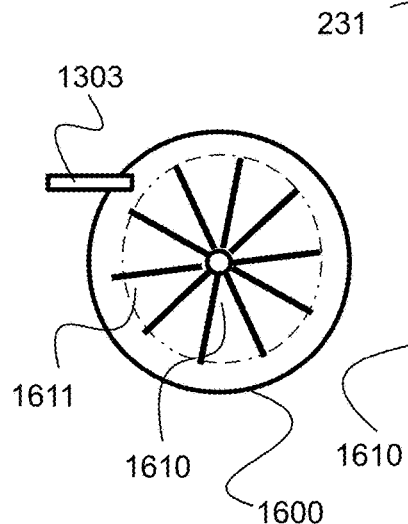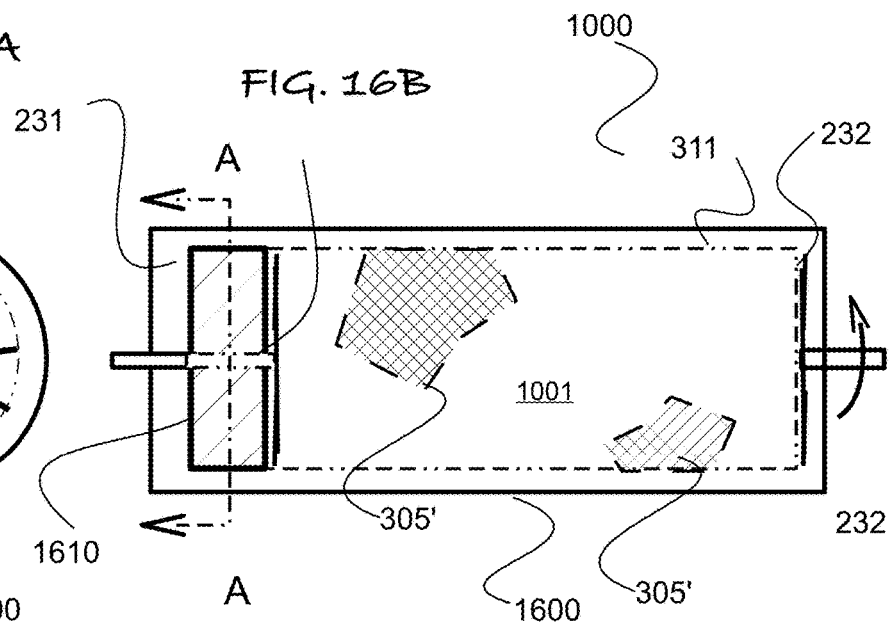

ROTARY SEPARATION APPARATUS AND PROCESS

CROSS REFERENCE TO RELATED APPLICATIONS

The present application is a Continuation-in-Part of and claims the benefit of priority to the U.S. Non-provisional patent application that was filed on Jul. 4, 2017 and having application Ser. No. 15/641,254, which in turn claims the benefit of priority to the US Provisional Patent Application that was filed on Jul. 6, 2017, having application No. 62/358,988 all of which are incorporated herein by reference.

BACKGROUND OF INVENTION

The field of the present invention is the extraction of resins containing organic compounds from resinous plants, and more particularly to the separation of resin from resin-bearing glandular trichomes bearing from plants buds and flower, which tend to be high in trichome as a weight and/or volume, as well lower weight resin bearing plant matter, such as leaves and stem materials.

A number of plant varieties produce commercially valuable isoprene derivatives and phenolic compounds such as terpenoids in cell assemblies know as trichomes or more specifically, in the glands of glandular trichomes. Portions of different plants are rich in trichomes containing compounds of interest in commercial and medicinal applications. Conventional extractive processes may not be adequate in preserving volatile and/or oxidation-sensitive compounds.

Conventional extraction and separation methods utilize solvents which may be polar, non-polar or combinations thereof in order to extract and separate desirable substances. Conventional extraction methods are expensive to conduct safely and may introduce undesired compounds by collateral extraction. Commonly extracted undesirable compounds may include pigments such as anthocyanin, chlorophyll, tannins, saponins and lipids from cellulosic materials.

Further, as plants mature, many glands of glandular trichomes increase in size, mass and chemical composition. Plant cells associated with the trichomes biosynthesize phenolic compounds including terpenoids such as cannabinoids and humulones. However, at harvest time, when the plant is deemed to have reached a peak in the content of desired compounds, trichome assemblies may be in a range of sizes. Trichome and trichome gland assemblies can be separated from the bulk of undesirable plant material by sieving procedures. Larger trichomes can be harder to separate from undesirable plant matter that does not contain desired chemical species.

However, as resin bearing trichomes are sticky, physical separation by dry or wet sieving processes are problematic because a large fraction of plant matter fragments of comparable size to the desired trichomes are generated from the mechanical force of agitation, chopping or grinding of the plant matter to release the desirable trichomes and/or trichome glands.

In any physical separation process, it is necessary to not only collect the resin product, but remove residue and clean the filter.

It is an object of the present invention to provide an improved process and device to remove residue and clean the filter, as well as collect the product under conditions discovered most conducive to rapid and efficient separation.

The above and other objects, effects, features, and advantages of the present invention will become more apparent from the following description of the embodiments thereof taken in conjunction with the accompanying drawings

SUMMARY OF INVENTION

In the present invention, the first object is achieved by providing a rotary axis separation apparatus comprising a chamber having at least one or more opening for adding and removing materials, a filter container adapted to rotate about an axis within the container, a means for introducing an inert freezing agent into the chamber.

A second aspect of the invention is such a rotary separation apparatus wherein the means for introducing the inert freezing agent is an inlet directed into the chamber.

Another aspect of the invention is any such rotary separation apparatus further comprising a fluid diverter means disposed in front of an inlet for the inert freezing agent.

Another aspect of the invention is any such rotary separation apparatus wherein the inert freezing agent is introduced directly into the filter container.

Another aspect of the invention is any such rotary separation apparatus wherein the inert freezing agent is a liquid freezing agent.

Another aspect of the invention is any such rotary separation apparatus wherein the inert freezing agent is introduced directly into the filter container and the fluid diverter means is disposed in the filter container.

Another aspect of the invention is any such rotary separation apparatus wherein the fluid diverter means is an inner wall of the container.

Another aspect of the invention is any such rotary separation apparatus wherein the fluid diverter means is one of than inner and outer wall of the filter container.

Another aspect of the invention is any such rotary separation apparatus wherein the fluid diverter means is a diverter cap disposed in front of an inlet for the liquid freezing agent.

Another aspect of the invention is any such rotary separation apparatus wherein the diverter cap has an inner wall configured to receive the inert freezing agent and opening on one or more sides of the inner wall for the diverted liquid freezing agent to flow outward laterally from the diverter cap.

Another aspect of the invention is any such rotary separation apparatus wherein the inner wall has a continuous curvilinear shape from a center portion to an outer periphery that forms the opening openings on the one or more sides of the inner wall.

Another aspect of the invention is a method of processing plant matter, the method comprising providing a mixture of plant matter that includes flowers and flower buds and at least one of leaves, bracts and bracteoles, in which the flowers and flower buds contain calyxes and sugar leaves, placing the mixture in a confined space, tumbling the mixture within the confined space, introducing an inert freezing agent into the confined space wherein residual moisture in the one or more of the leaves, bracts and bracteoles freezes causing the fragmentation thereof such that a resulting fragmented plant matter is smaller in size than the flower buds.

Another aspect of the invention is such a method of processing plant matter wherein the confined space has a plurality of opening such that the fragmented plant matter traverses the openings and the confined space retains a residual portion of the flowers.

Another aspect of the invention is any such method of processing plant matter further comprising providing an outer container around the confined space to collect the fragmented plant matter.

Another aspect of the invention is any such method of processing plant matter wherein the inert freezing agent is a liquid freezing agents.

Another aspect of the invention is any such method of processing plant matter wherein the liquid freezing agent is one of liquid carbon dioxide and liquid nitrogen and a liquid noble gas.

Another aspect of the invention is any such method of processing plant matter wherein the inert freezing agent is introduced to one of the outer container and the space as a jet and the jet is diverted to broadly distribute the liquid freezing agent to preclude direct impact of the jet with the plant matter within the confined space.

Another aspect of the invention is any such method of processing plant matter wherein the plant matter is from the species of lupus or cannabis and the residual portion of the flower is primarily calyxes.

Another aspect of the invention is any such method of processing plant matter wherein the fragmented plant matter includes one or more of fan leaves and sugar leaves.

Another aspect of the invention is any such method of processing plant matter wherein calyxes remain intact as the fan leaves and sugar leaves are fragmented.

Another aspect of the invention is any such method of processing plant matter wherein the confined space is bounded on at least one side by a mesh member, wherein the mesh member has opening of a size sufficient to retain the mixture of plant matter in the confined space.

Another aspect of the invention is any such method of processing plant matter wherein the mixture within the confined space is tumbled by agitating a support member for the mesh member.

Another aspect of the invention is any such method of processing plant matter wherein the support member is agitated by rotating about an axis thereof.

Another aspect of the invention is any such method of processing plant matter wherein the support member is rotating by directing the jet of the liquid freezing agent against the support member.

Another aspect of the invention is any such method of processing plant matter wherein the support member is coupled to a turbine blade assembly that receives the jet of liquid freezing agent that is operative to rotate the turbine blade assembly and the support member.

The above and other objects, effects, features, and advantages of the present invention will become more apparent from the following description of the embodiments thereof taken in conjunction with the accompanying drawings.

BRIEF DESCRIPTION OF DRAWINGS

FIG. 1A is a perspective view of the separator with the lid in place, whereas FIG. 1B shows the inside of the lid in a removed inverted position from FIG. 1A.

FIG. 2A is a top perspective view of the lower portion of the separator with the lid removed to illustrate an embodiment of the frame, whereas FIG. 2B is a perspective view of the separator showing the frame and lid removed.

FIG. 5A is a perspective view of an embodiment of the filter installed over the frame while

FIG. 8A is a side elevation view of another embodiment of the filter, while FIG. 8B is a cross-sectional elevation view of a portion of the filter that attaches to the frame, whereas FIG. 8C illustrates the filter in a disassembled condition in a plan view.

FIG. 10A is a perspective view of an internal filter bag whereas FIGS. 10B and 10C illustrate in a perspective view and cross-sectional view respectively how the bag is mounted within the frame to be surrounded by the larger filter that fits over the frame.

FIG. 13A through C are orthogonal sectional views of another embodiment of the apparatus, whereas FIG. 13D is a sectional elevation view of another embodiment, all of which deploy a means for diverting the flow of liquid freezing agent.

FIG. 14A-D illustrate alternative embodiments of the diverter cap that may be deployed in the embodiments of FIG. 13A-D, in which FIGS. 14A and 14B are respectively side and front elevation views of one embodiment. FIGS. 14C and 14D are respectively side and front elevation views of another embodiment of the diverter cap.

FIG. 15A-15E schematically illustrate other embodiments of a liquid freezing agent diverter for use in the novel processes, in which FIG. 15A is a sectional elevation view of a horizontal axis separation apparatus and FIG. 15B/C and FIG. D/E are respectively sectional elevations and plan view of the flow patterns with 2 alternative embodiment of vertical axis rotary separation apparatus'.

FIG. 16A-D illustrate alternative embodiments of the invention for using a liquid freezing agent as a means to agitate plant matter container in a confined space in which FIG. 16A is a cross-section elevation of the apparatus at section line A-A in the elevation sectional view of FIG. 16B. FIG. 16C is a cross-section elevation of another embodiment of the apparatus at section line C-C in the elevation sectional view thereof in FIG. 16D.

DETAILED DESCRIPTION

Figure 3A:
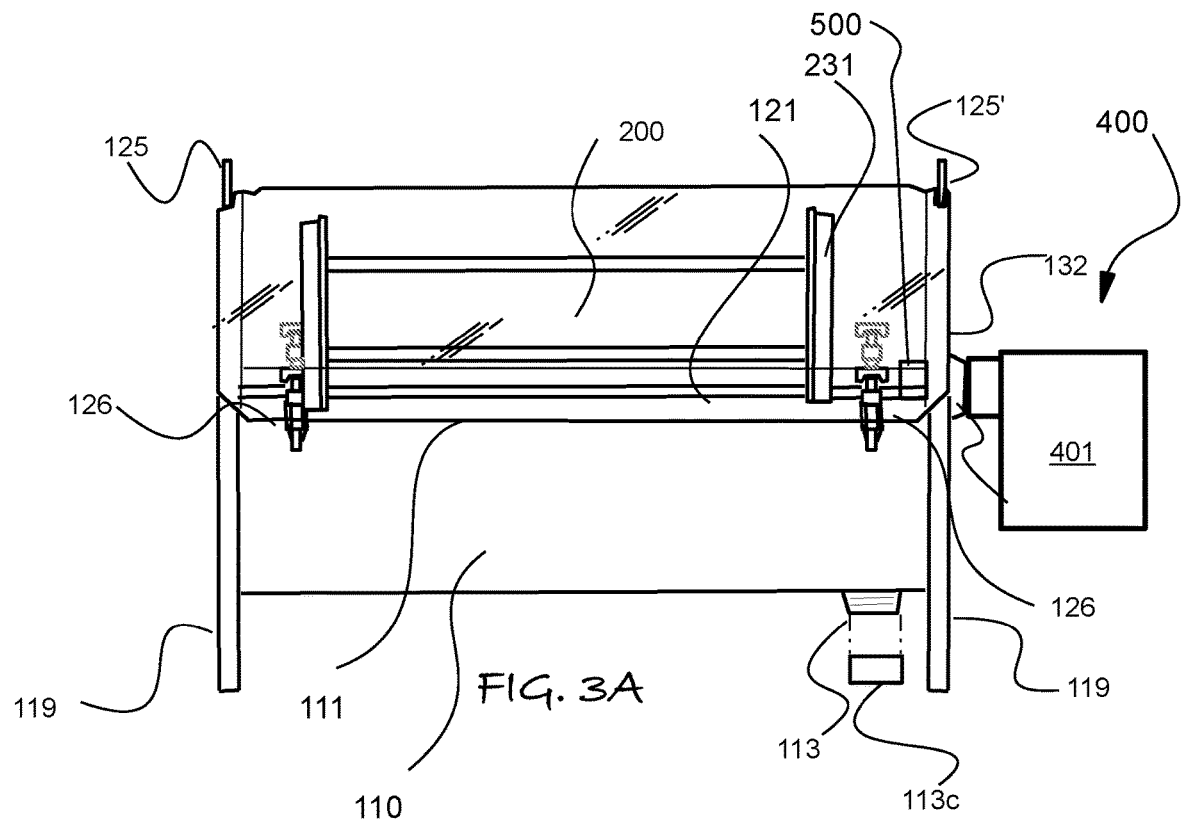
FIG. 3A is a side elevation view of the separator with a transparent lid.

Referring to FIGS. 1A through 16D, wherein like reference numerals refer to like components in the various views, there is illustrated therein a new and improved Rotary Separation Apparatus and Process, generally denominated 1000 herein.

In accordance with an aspect of the present invention the horizontal axis rotary separation apparatus 1000 may comprises a chamber 100 which may have a half cylindrical basin 110 having an upper rim 111 and a half cylindrical lid 120 having a lower rim 121. The basin 110 preferably includes at a bottom a drain portal 113 to remove fluid used in the separation process and/or the resinous product of the separation process. The basin 110 is preferably disposed above a support surface by feet or frame edges 119. In such an embodiment the chamber 110 is cylindrical. However, the chamber 110 can be other shapes so long as it accommodates the internal rotating filter support frame 200, described further below. Other aspects of the invention will be described with respect to the preferred cylindrical chamber 100.

A pair of side end plates 131 and 132 is connected to opposing ends of the basin 110 and extends upward above the upper rim 111 thereof. The lid 120 is configured to fit over the edge of the side plates 131 and 132 so the straight side of the lower rim 121 meet the corresponding straight sides of the upper rim 111 and generally provide a closed cylindrical cavity 1001. The sides 131 and 132 may have upward extending handles 125 and 125'. The lid 120 preferably has handles 125L just above the opposing lower rims 121. Handles 125 and 125' are also optionally placed on the adjacent portion of the lid 120, as illustrated when the lid is inverted in FIG. 3B. In either embodiment, the lid 120 may also have handles 125L just above the opposing lower rims 121. The junctions between the basin 110 edges and the edges of the side end plates 131 and 132 that mate with the edge of the lid are preferably at least partially sealed during processing with a gasket or conforming elastic material, which is optionally discrete pieces of conventional weather stripping material.

The cylindrical cavity 1001 between the basin 110 and lid 120 also contains a rotating filter support frame 200. The filter support frame 200 has attached spaced apart support disks 231 and 232 that are connected by a series of posts 240 to form a rigid support assembly. Three or more posts 240 extend about the periphery 231p of each disk 231 and 232 to form a rigid support for a generally but not exclusively flexible filter bag member 300, of which an embodiment is illustrated in perspective view in FIG. 3A. The support frame 200 optionally includes a central post or support 241, which in select embodiments provide a conduit to 241b feed fluid, such as gas or liquid into the cavity 1001 via side holes 241h to aid in the separation process. Post 241 is disposed along the cylindrical axis of the frame 200, which becomes the rotary axis in the process of separation.

The rotating filter support frame 200 is adapted to rotate about a cylindrical axis 201 of the device 1000 and the cylindrical cavity 1001. A rotary drive means 400 is adapted to couple to at least one end of the rotary support frame 200. The filter frame support 200 has portions 242 and 243 that extend beyond spaced apart support disks 231 and 232 that engage a rotary drive couplings 500 supported by the by the side plates 131 and 132. At least one of the rotary drive couplings is preferably a rotary bearing with an intermeshing or rotary tooth structure 410 at one side to engage a complimentary structure in the outward extending portion 242 or 243. The rotary drive means 400 is coupled to the rotary tooth structure 410, such as by a drive shaft that is support by a bearing at the interface to the side plates 131 or 132. The opposing side plate also has a rotary bearing for supporting the other extending post 242 or 243. The rotary tooth structure 410 is preferably disposed inside the cavity 1001. It is also preferably to deploy a rotary bearing and quick disconnect on one end outside of support disks 231 or 232.

The removable filter member 300 extends over the support frame 200 and is adapted to be filed with plant matter from a side opening having a zipper 310. In the process of use, plant matter is inserted in the removable filter member 300 and with the lid 120 removed. The lid 120 is closed to seal the cavity 1001 and the latching hinges 126 are engaged to secure the lid 120 in place. Then the filter support 200 is rotated by the rotary drive means 400. Plant resin particles escape through the filter openings and tumble to the bottom of the basin 120. The lid 120 is opened and the rotary filter support frame 200 is removed from the rotary coupling, such as the rotary tooth structure 410 in the lower cylindrical base 120, and then placed in the inverted half cylindrical lid 120. When the frame 200 is removed solid product is optionally removed from the bottom of the basin 120 via the rim 121, or via the drain portal 113. Fluid can be used to continuously flush product through the drain portal 113.

Figure 3B:
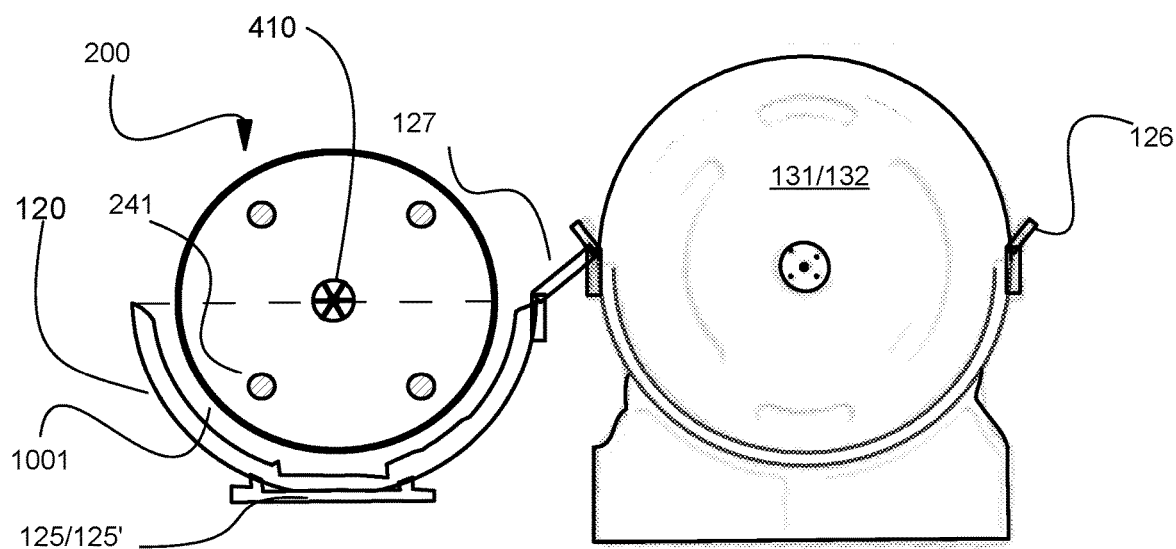
FIG. 3B shows the separator in an orthogonal side elevation view with the lid open and inverted.

In a more preferred embodiment illustrated in FIG. 3B, the lid 120 is in hinged engagement to the side of the basin 120 to provide a work station for removing and replacing the filtered plant matter with new plant matter while the product is being removed from the basin 120. As illustrated in FIG. 3B, the latches on one side of the rim 111 are preferably double axis hinges 127 to space the upper shell or lid 120 laterally away from the lower shell or basin 110. The lid 120 has handles 125 and 125', which support the lid 120 in the inverted position used to support the filter member 300 as disposed over the support frame 200. The rims 121 and 111 opposite the hinges 126 and 127 are connected by clamps prior to engaging the rotational drive means 400.

Another aspect of the invention are preferred and alternative embodiments of the removable filter member 300, which are adapted to fit over the rotating filter support frame 200, which more particularly can be readily removed or replaced from the support for cleaning or maintenance, or simply to facilitate the removal of spent plant matter after resin product is removed.

It should be appreciated that the filter member 300, such as is illustrated in FIG. 4A-4D, is a generally cylindrical mesh bag generally conforming with the shape of the frame 200 to fill cavity 1001, but configured to not interfere with the rotation of the frame 200, as well as to provide a tight seal to the support disks 231 and 232 for maintaining plant matter therein during the separation process. The bag or filter 300 has a rectangular central portion 305 that is formed into a tube sealed by circular ends or bases 331 and 332. As illustrated in FIGS. 5A and 5B, when the filter 300 extends over the support disks 231 and 232 the circular ends 331 and 332 are preferably annular to provide an aperture 335 for extending post 242 or 243. The annular ends 331 and 332 are optionally tightened over the support disks 231 and 232 by a cinch cord 383 or elongated elastic member that passes through a channel formed in the inner annular end of each of end 331 and 332. The filter member on the support frame 200 defines within the closed interior surface thereof and disks 231 and 232 a container or containment vessel 311 for materials to be processed of which a smaller component, or a component produced or released during processing will exit the container 311 and enter the surrounding portion of the closed cylindrical cavity 1001, for eventual collection with the lid and filer frame 200 removed or by exiting by drainage port 113. It should be appreciated that in the context of some embodiment, the container 311 need not be perforated or have any mesh portions, and the material may optionally also be processed directly in any container that provides a bounded cavity 1001.

In some processes of use it is desirable to add fluid or gases in to cavity 1001 or the container 311 while the cover is in placed and optionally when the support frame 200 is turning or rotating. Such inlet for fluid and gases can be in the center of the end 131 or 132, passing through the adjacent end of disk 231 and 323 at the center thereof to introduce gas or fluid into the container 311 to aid in the processing of the matter therein. Fluid can be introduced by the same method or any other penetration in the chamber 100 to flush material that then exits the container 311 via the drainage portal 113.

It should be appreciated that the longitudinal side zipper 310, which is deployed for side filling access to the frame supported filter 300, can be replaced with an alternative sealing means, such as loop and hook fasteners, button, loops, snaps and the like. Side zipper 310 is generally formed by attaching the engaging side teeth 310a and 310b at sides 301a and 301a' of the rectangular screen or mesh sheet 305.

Figure 6:
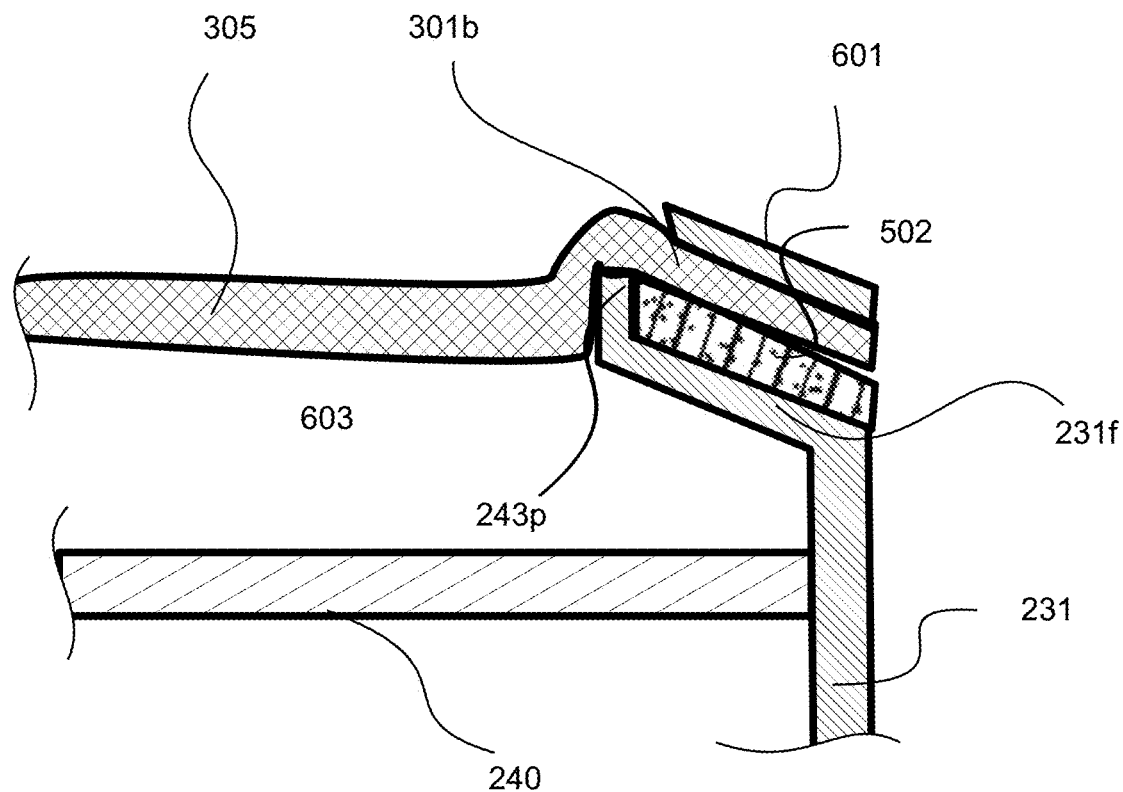
FIG. 6 is a cross-sectional elevation view of another embodiment of the filter shown attached the ends of the support frame.

As shown in FIG. 6, the filter 300 can be formed by attaching the rectangular filter sheet 305 to the annular flange like ends 231f of the disks 231 and 232 by a clamp means, such as a strap or tightened belt member 601 that compresses the edge 301b of the rectangular sheet 305 into a foam member 502 that is either adhered to or supported by disk 231/232. The compressed foam 502 prevents leakage of product from inside the filter 300 at edges 301b and 301b'. The ends of the belt 601 can be attached with a buckle, hook and loop fasteners, snaps and the like.

Figure 7:
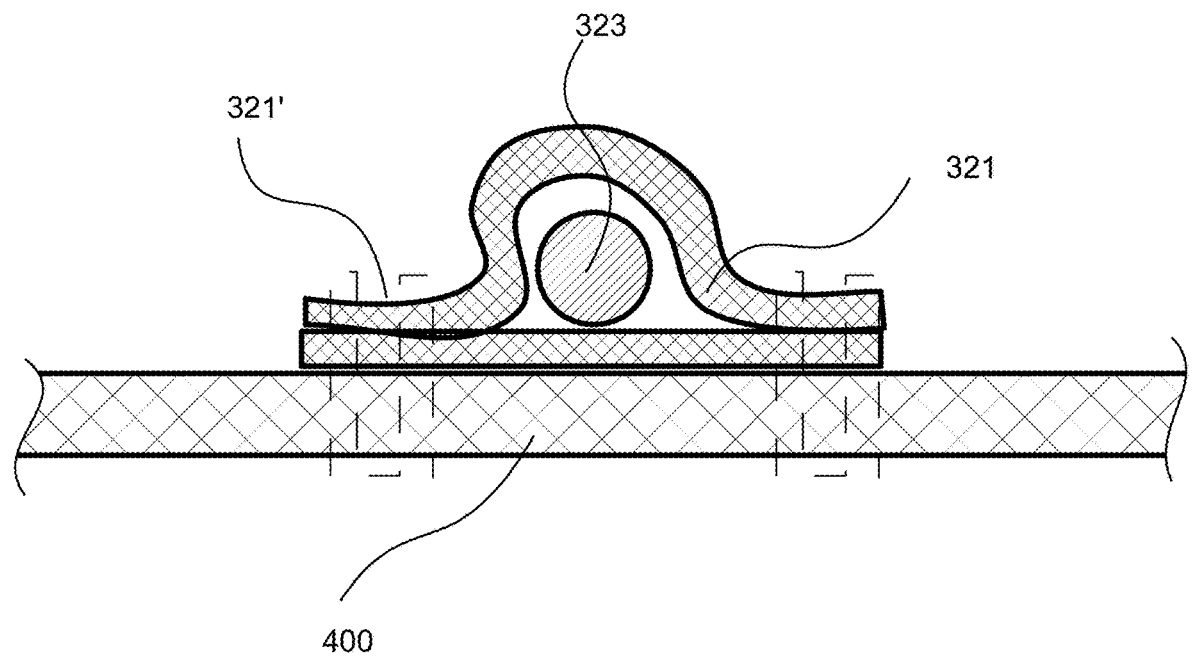
FIG. 7 is a cross-section elevation view through a central portion of the filter that is transverse to a cord showing the surrounding reinforcing strip.
Figure 8:
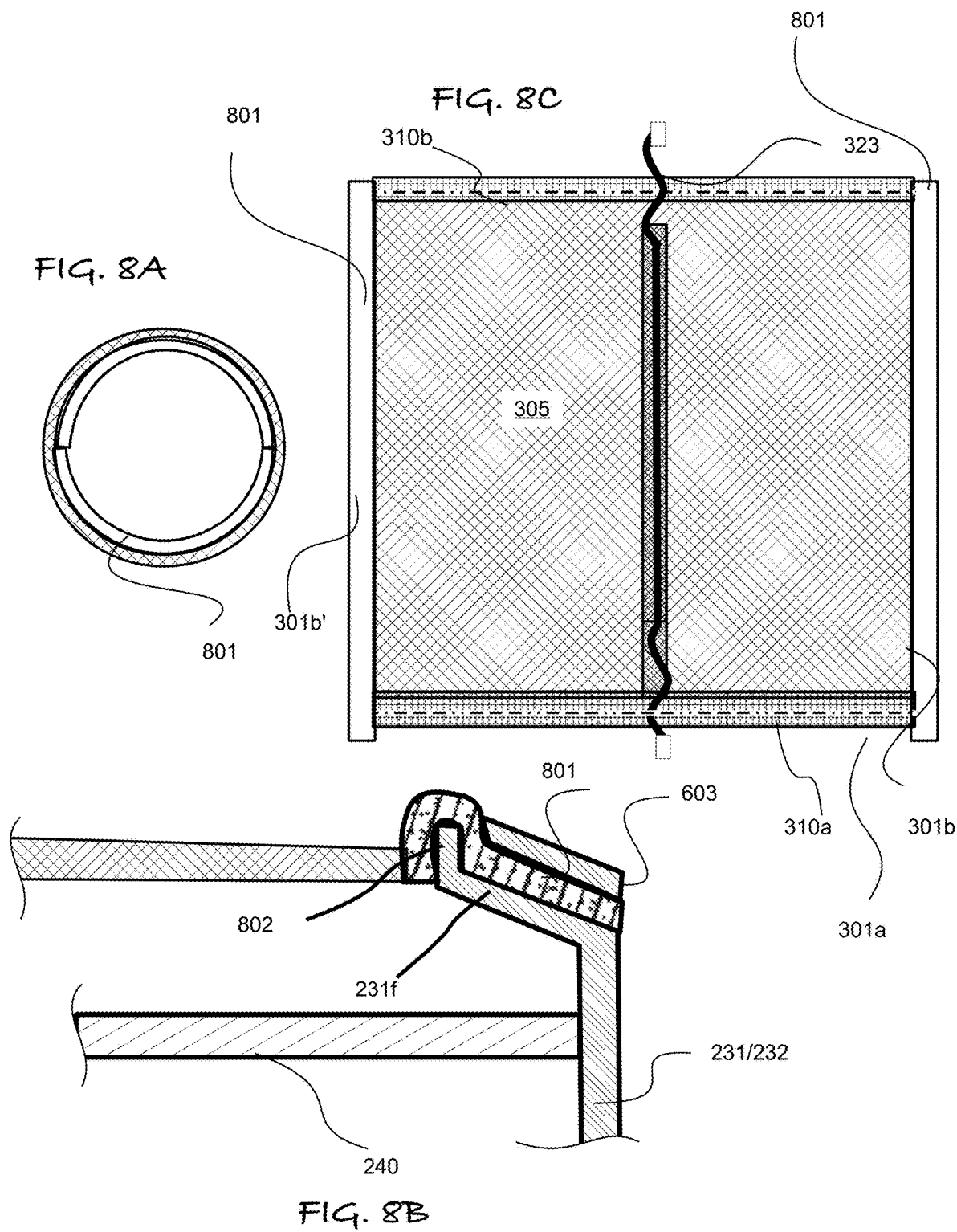

The filter member or bag 300 of FIG. 4-6 has the aforementioned zipper 310 along a longitudinal side may also include one transverse reinforcing band, such as a fabric strip 320 extending around the circumference of the bag disposed between opposing ends. As shown in FIG. 7, the fabric strip 320 is preferably two adjacent strips 321 and 321' sewn together at the edge to the mesh 305 to form an interior channel that receives an elastic cord 323 that is tightened when the zipper 310 is closed. The cord 323 is tightened by drawing the opposing ends through a common clamp member that is closed. It should be appreciated that all zipper pulls preferably have a means to be secured in a closed state, such as a locking zipper, button, snap, loop and hook fabric cover and the like.

Another configuration of the filter 300 is shown in FIG. 8A-C in which a rectangular sheet 305 with side zipper 310 halves at sides 301a and 301a' has attached at each orthogonal ends 301b and 301b' a pairs of clamps members 801, each having a groove 802 adapted to snap into the end support disks 231/232 of the filter support frame 200. A belt 803 is wrapped around the flat portion of the gasket 802 to and tightened around the flange edge 231f such that the filter 300 and support frame 200 becomes an integrated unit. The ends of the belt 803 can be attached with a buckle, hook and loop fasteners, snaps and the like.

Figure 9:
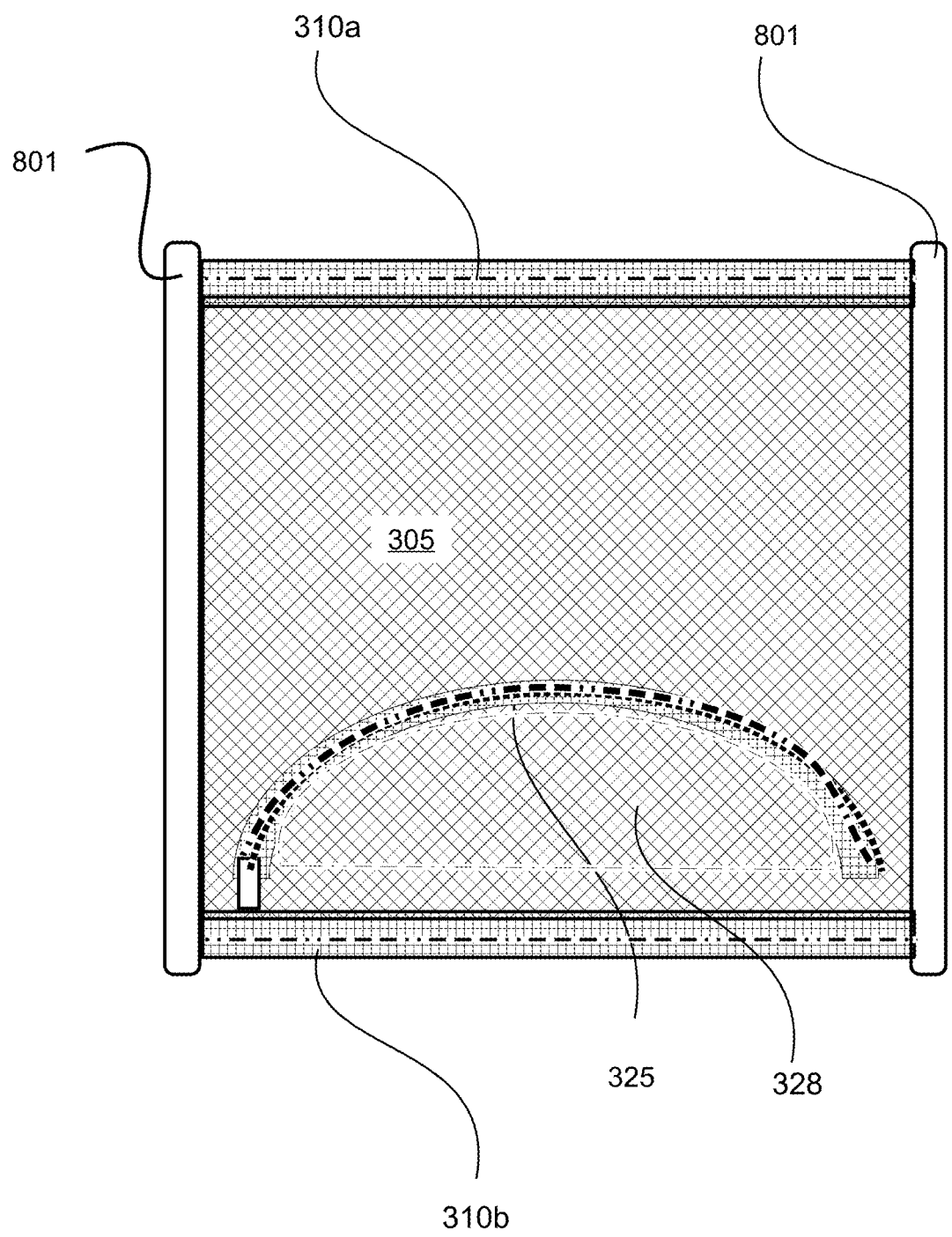
FIG. 9 is a plan view of a portion of another embodiment of the disassembled filter.

FIG. 9 is a top plan view of the filter 300 as in FIG. 8A-C, with a second curved zipper 325 that enables side access to the filter screen sheet 305 when installed integral to the frame 200 via ends 231 and 232, such as when disposed as shown in FIG. 3B, or within the cavity 1001.

It should be appreciated that the posts 240 of the support frame 200 also aid in stirring, tumbling and agitating the plant matter mixture during the separation process, preventing clumping that would lower extraction efficiency and yield. Depending on the nature of the plant matter, and the size of the separation device 1000, the number and shape of the support posts 240 may be varied to further minimize the potential for such clumping. For example, the support posts 240 also may have axially radiating planar fins, cylinder and related protuberances beyond the primary envelope of the post's circular or non-circular shaft diameter to better facility agitation, mixing, tumbling and mechanical disintegration of plant matter to release resin bearing trichomes The drain 113 can also have an external screw thread to accept a removable internally threaded cap 113c, and this cap 113c can be replaced with a hose via a threaded hose coupling to direct the flow of product to different containers or control the output flow rate via valves, such as to match the input rate of rinse water or other fluid.

It should also be appreciated that the outer housing 110 and cover 120 can deviate from the generally cylindrical shape, as can the inventive filter support assembly 120 that is rotated therein. For example the housing 110 and cover 120 can be an elongated member with any shape linear and curvilinear cross section, including rectangular and square.

The inventive device can also be used to produce compost tea by a least partially filing the chamber portion 12 with water and filing the filter enclosure 300 with composted materials. After sufficient brewing of the compost with agitation by rotating the filter 300 the composted tea is drawn out of the lower exit portal or drain 1131, which during the soaking process, is closed with a valve, cap or plug 113c.

Figure 4A:
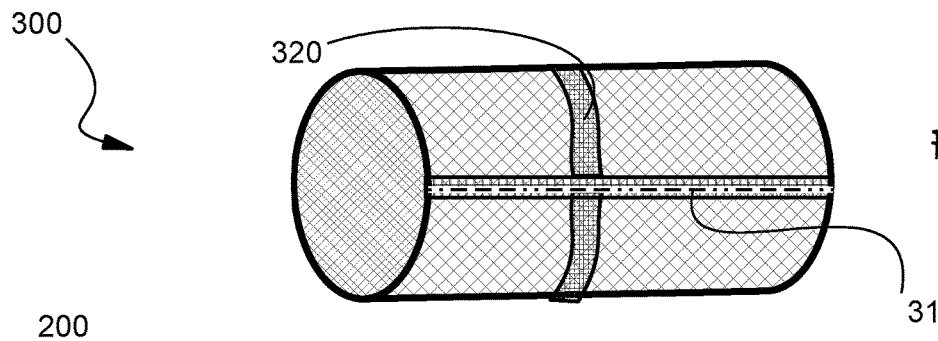
FIG. 4A is a perspective view of an embodiment of the filter, with FIG. 4B illustrating the frame, and FIG. 4. C showing the filter installed over the frame.
Figure 4B:
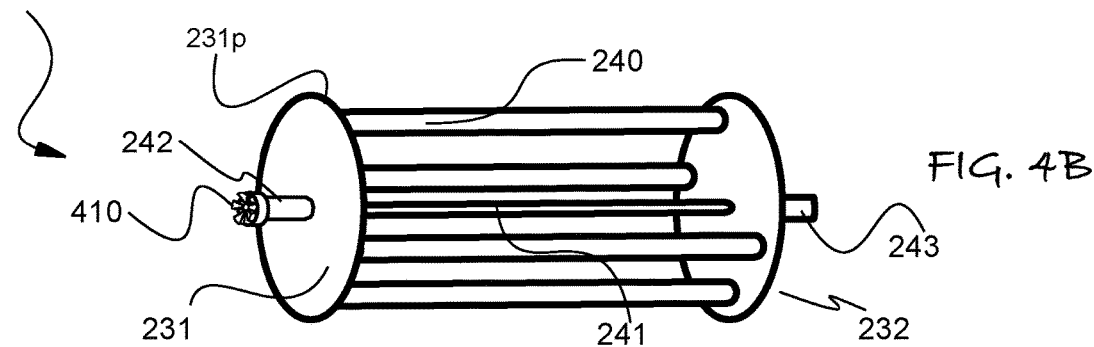
FIG. 4D illustrates the filter in a disassembled condition in a plan view.
Figure 4C:
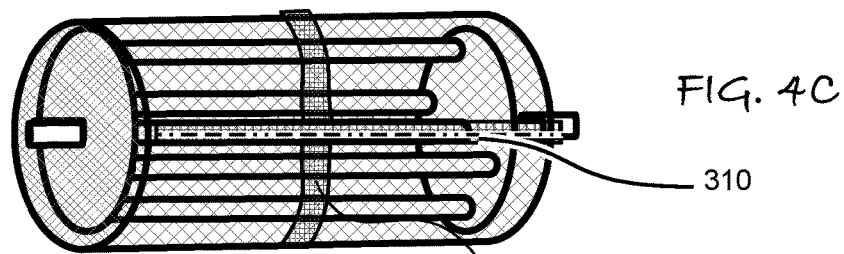
Figure 4D:
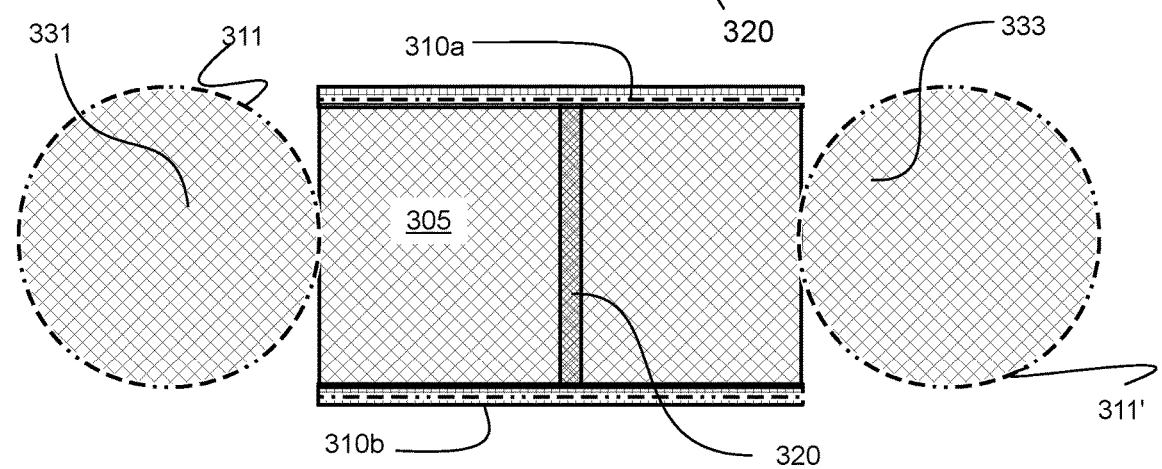
Figure 5A:
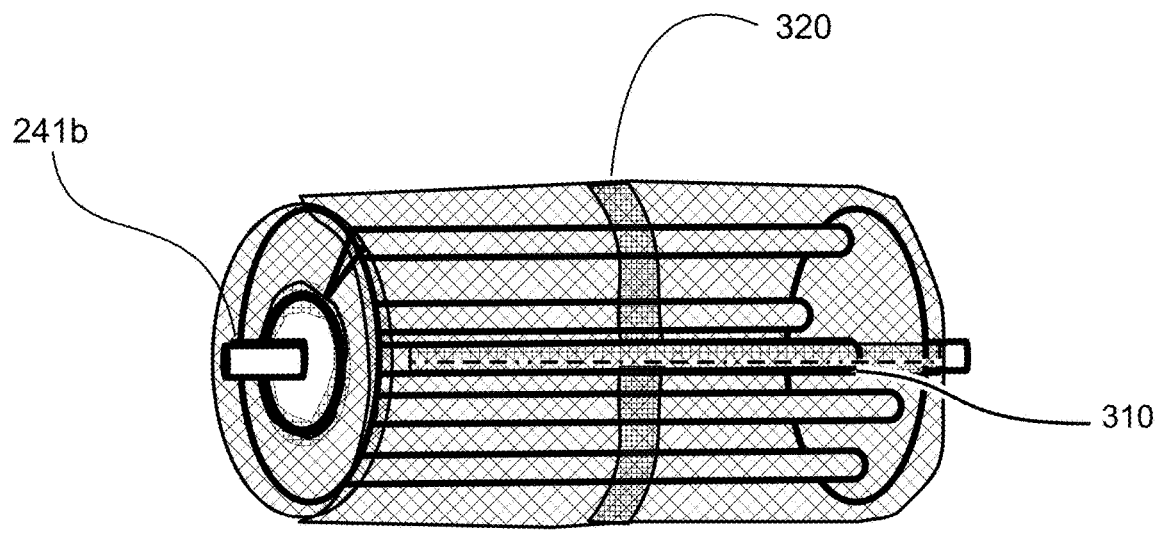
Figure 5B:
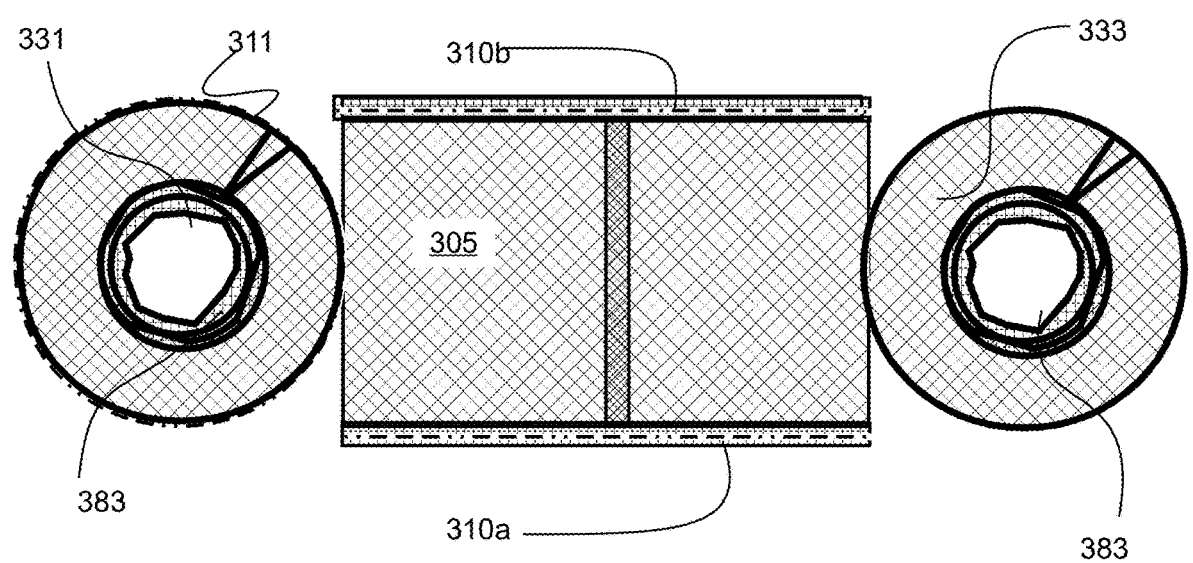
FIG. 5B illustrates the filter in a disassembled condition in a plan view.

The strap or tightened belt member 601 can be used with the other embodiments of the filter 300, and beneficially reduce stress on the primary or side zipper 310, in the embodiment of FIGS. 4d, 5b and 8c, which depending on the size filter can minimize or eliminate the needs for the circumferential cord 323.

The second zipper 329 of FIG. 9 facilities loading and unloading of plant material, as it avoids the strain on the filter bag 300, which would occur if the primary zipper 310 is opened when the separate sides at zipper halves 310a and 310b are pushed away. Further, it facilitates creating a larger opening, as the area circumscribed by the zipper arc 328 opens as a flap.

FIG. 10A is a perspective view of an internal filter bag 701 whereas FIGS. 10B and 10C illustrate in a cut-away and cross-sectional view respectively how the bag 701 is mounted within the frame 200 with hooks 705 to be surround by the larger filter 300 that fits over the frame support 200. Bag 701 is a mesh filter with a zipper closure 710. When the outer filter 300 has a finer mesh than the bag 701, the resulting resin particles of a given size are containing within the filter 300, and the bags 701 are repeatedly filled with plant matter until the resin in the filter 300 is ready for removal from the separator 1000.

Figure 11:
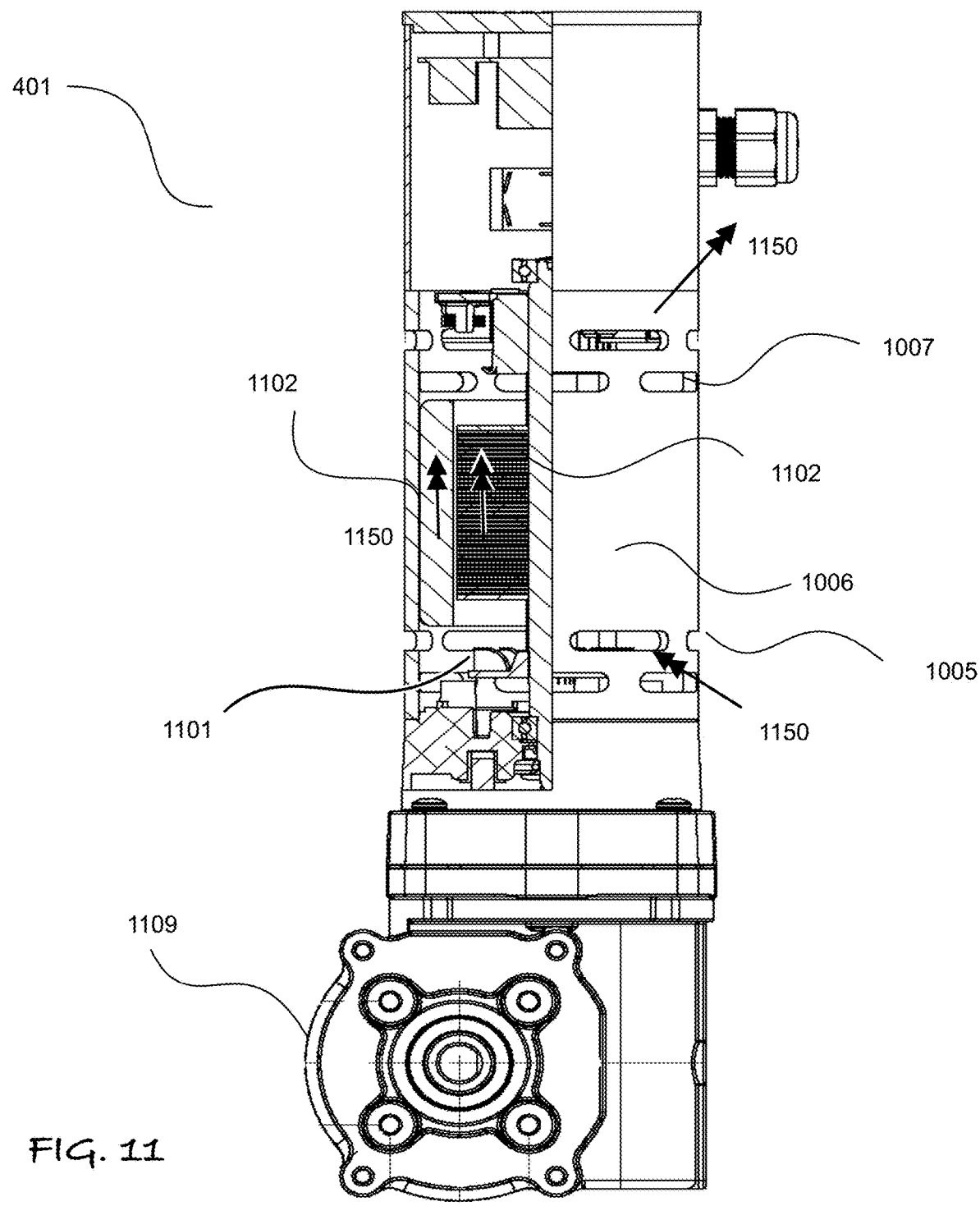
FIG. 11 is a partial cut away elevation view of a preferred embodiment of the motor.

FIG. 11 is a partial cut away elevation view of the preferred embodiment of the drive motor 400 that is a multi process capable motor with wide speed and torque range and motor cooling features. By multi-process we mean capable of carrying out the aforementioned separation processes either dry or wet using an added fluid (generally water, but also ice water slurries) or with the assistance of gas, including adiabatic expansion of carbon dioxide gas to form "dry ice" crystals. The motor's rotor 1103 and stator 1102 are cooled to prevent over heating during use by the fan blades 1101 that coupled to the motor drive shaft, with the fan blades adjacent to intake apertures 1005 formed in the motor housing 1106. The drive shaft that supports the rotor 1103 is connected to the filter support coupling via a gear box 1109. Arrows 1150 show the direction of air flow around the rotor 1003 and between the stator 1102 from the lower intake apertures 1005 to exit at the upper apertures 1007. The forced air cooling is important for providing a single motor that can accommodate the range of speeds and torques needed in the potential separation processes noted above.

The inventive apparatus can be used to separate a wide range and type of materials. Many plant and herb species have the highest concentrations of terpene and cyclic terpene bearing aromatic and medicinal resins in the flowering portions of the plant, and in particular in glandular or secreting trichomes. The flowers typically form at the tips of growing shoots. The flowers, flower buds and leaves have hair like outgrowths that are referred to as trichomes. These trichomes being glandular secrete plant resins as a small bulb or head at the end of a stalk like hair.

A range of methods have been developed in attempts to efficiently and economically process Cannabaccae plant matter to extract glandular trichomes to yield high concentrations of the resin by separating the plant matter acquired in the harvesting of the flowers, flower buds and leaves from cannabis plants. Some prior art sieving method use water as a medium to suspend the plant matter, while other methods sieve the plant matter without water, while others do so in the dry state. Generally speaking, such wet or water based sieving extraction processes for Cannabaccae trichomes yield an inseparable mix of desirable trichomes and undesirable plant debris, based on size as well as the duration and intensity of agitation. Such a process is generally disclosed in the International Patent Application with publication no. WO 2014/00919A2 (to J. P. Love, which published (January 2014), and is incorporated herein by reference. Another prior art separation method is disclosed in issued U.S. Pat. No. 8,640,877 (Pastorius, Feb. 4, 2014) for a pollen separator, which is incorporated herein by reference. Various raw plant materials are processed via such a water and ice agitation method. It further suggests that small diameter mixtures of plant pollen and plant debris are separated by eight sieves, having progressively smaller holes from 220, 190, 160, 120, 90, 73, 45 to 25 microns. However, the patent is silent on separating the desired pollen or other components from plant debris of the same size, other than by solvent extraction. Similarly, U.S. Pat. No. 4,051,771 (Miyata, et al., Oct. 4, 1977), which is also incorporated herein by reference discloses an apparatus for obtaining lupulin-rich products from hops, in which lupulin glands or trichomes are extracted by a combination of crushing and dry sieving in a frozen state.

The inventive apparatus can be used to separate the trichomes from various plant and herb species. The method of using the apparatus and variants on the apparatus that might be already known to one of ordinary skill in the art can be adapted to improve the separation rate and efficiency for a particular plant species depending on the separation objective. For example, the inventive apparatus can be used in different ways to obtain either the isolated trichomes, or plant matter having the highest concentration of trichomes. The tips of growing plans that are beginning the flowering process may have multiple flower buds or flower interspersed with fine leaves. These fine leaves are known as bracts and bracteoles. In the case of cannabis and related species, such as hops, the flower region contain multiple buds, also known as calyx's, as well as pistils, seeds, bracts and bracteoles. The bracts and bracteoles in Cannabis are referred to as sugar leaves. While the sugar leaves have higher concentrations of trichomes and the desirable resins than larger or bigger leaves, often referred to as palm leaves, which are lower down the shoots from the flower region, the highest density of trichomes and hence concentration of resins are in the calyx's and pistils of the flowers and buds. Thus, it is desirable in processing Cannabis plants to isolate the flowers from plants, but remove the seeds, if any, and sugar leaves. These sugar leaves, when removed or "trimmed" are frequently referred to as "trim". Another aspect of the invention is a method of rapidly removing the "trim" or "trimming" while leaving the other desirable portions of the plant, which is the flower and buds largely intact.

Another aspect of the invention is further processing the "trim" to extract and isolate the trichomes there from. In such a process it is also desirable to minimize the extraction of cellulosic debris from the trim, as well as leaf cells components, such as chlorophyll.

Another aspect of the invention is further processing the intact flowers and buds to extracts the trichomes and produce a plant resin right concentrate.

It is a common practice in harvesting Cannabis to cut growing shoot or stalks having palm leaves and flowers, and then dry these shoots or stalk. The palm leaves can be removed, such as by cutting or manual pulling, before or after drying. The sugar leaves are typically removed after drying.

Another aspect of the invention is a method for trimming sugar leaves, other leaves and other undesirable plant matter from the entire plant without drying. This avoids the need for extend facilities and spacing for the drying process, which takes days, as well as the manual labor in material handling. Another aspect of such a process is that it can produce a Cannabis extract that retains essentially all the Cannabidiol (CBD) produced by the plants. CBD is one of at least 113 active cannabinoids identified in cannabis and can account for up to 40% of extracted plant resin. However it deteriorates rapidly with further processing, such as drying of the plants. CBD does not have any intoxicating effects and is component of several drugs under development or undergoing regulatory approval. Further, since such a Cannabis extract will also contain the A form of tetrahydrocannabinol (THC), which is not psychoactive (in contrast to the $\Delta^9$ form of THC) it can be used for medicinal purposes without the need to separate the THC. The A form of THC converts to the 49 form rapidly as freshly cut Cannabis plant matter starts to dry.

The preferred modes of conducting these processes are described below with respect to versions of the inventive apparatus in which the filter 300 as supported on the support frame 200 has an internal capacity or volume of about 5-20 gallons, which respectively can be used to contain and process about 3-15 lbs. of plant matter, in the case of Cannabis, as well as any other plant species in which the glandular trichome produce resin that is desirable to separate for further processing or direct use. To accommodate such loads of materials and sizes support frames the motor can have a speed range of about 10 to 40 RPM. A preferred apparatus has 3 discrete speeds of 15, 25 and 35 rpm, and deploys a motor that is capable of providing the same torque at these speed to accommodate partially filling the chamber with water or another liquid, that is up to about 5-15 gallons, as well as the above weights of plant matter. More preferably the motor is capable being selectively operative to spin in opposite directions, and not in just a single direction.

It has been discovered that for the above capacity ranges, rotation speeds lower than about 10-15 rpm are not effective, while speed higher than about 35-40 rpm apply excessive centrifugal force. This excessive centrifugal urges the plant material toward the filter member 300 where it is retained. It is desirable to deploy a speed range in which the plant matter mixes and tumbles with each rotation of the filter member 300. It should be appreciated that various embodiment of the invention do not particularly preferred mesh bag construction 305 to form the filter member 300 or the container 311.

The mixing and tumbling are beneficially enhanced by several means. One such means is the spacing of the posts 240 of the support frame 200 as described above. Another means to improve agitation, mixing and tumbling is to add discrete pieces of non-plant matter that is inert and durable. Golf ball sizes spheres with a diameter of 0.5 to 2 inches are effective. In particular ordinary golf balls have both the desired size and density, which is mass, as well as inertness to be used in the various separation processes disclosed herein. It has been discovered that about 3 to 6 golf balls or similar size tumbling agent are effective in a 5 gallon chamber, while about 6-9 are effective in a 20 gallon chamber. The tumbling aids should not be so hard and/or massive that at the desired speed they would damage the material that forms the filter 300. The balls or tumbling agents' aid not only in breaking up material but also liberates any buildup of trichomes on the mesh or screen.

In a preferred embodiment of the trimming process, while the plant matter is tumbling within the closed space of the filter 300, an inert freezing agent (such as one of carbon dioxide ($CO_2$), nitrogen or a noble gas in one or both a liquid and gaseous state), is introduced therein in a quantity, rate and volume sufficient to rapidly reduce the temperature to about zero ° F., but more preferably about 10° F. to about 30° F. When an inert freezing agent, such as liquid carbon dioxide is introduced at a temperature of about −100 to −110° F. this temperature drop occurs in about 20 seconds to 2 minutes.

Not wishing to be bound by theory, it is currently believed that the rapid temperature drop from injecting inert liquid or gaseous freezing agent rapidly freeze residual moisture in the one or more of the leaves, bracts and bracteoles causing the fragmentation thereof to separate it from the desirable portions of the plant matter, which are the buds and flowers. It also appears that such an injecting of an inert liquid freezing agent will also purge air and oxygen as the liquid warms and expands as a gas. When the filter 300 has mesh opening of about ¼ in. to ½ in, this fragmented plant matter on continued tumbling then traverses the mesh opening of the filter while the filter 300 retains a residual portion of the flowers. Under the above conditions in a 5 and 20 gallon capacity chamber about the time of the trimming process is on the order a minute per pound (454 gm) of plant material, depending on the temperature in the chamber. At the lower end of the preferred temperature range, the trimming can be completed in as little as 30 seconds, in liquid freezing agent trimming for a is preferred, but can occur in 30 sec. but in cases of overfilling a container the inability to reach and hold a lower temperature can extend the process time to circa to 20 min. per lb. of plant matter. It is preferred that the chamber has a thermal measurement means to measure the drop in temperature during this process, and optionally control the flow of the inert freezing agent to maintain this temperature for a time sufficient to complete the process and extract the undesired plant matter.

The use of liquid freezing agent is more preferred as it also removes surface molds and fungus, and is believed to kill *E. coli* bacteria. The expanding gas from warming any liquid freezing agent also purges oxygen, preventing degradation of the cannabinoids during processing, and in the case of freshly cut cannabis, that is uncured plant matter, also prevents the conversion of the A form of THC to $\Delta^9$ THC, as well as the loss of the desirable CBD and potentially other cannabinoids of medicinal value. It may also be preferable to then dry freeze the product to prevent oxidation in handling, transport or storage, as this preserves the plant resins that are extracted before they can oxidize as they warm up in air. Flowers and buds that are freeze dried can then be stored at room temperature without oxidation and have a pleasing natural appearance.

It been discovered that after such trimming to remove sugar leaves, the residual flowers can then be processed again by changing the filter 300 to one having a smaller mesh size of less than about 25 to 200 or 300 microns to separate the trichome glands that are swollen due to the large resin content from the cellulosic plant matter in the buds and flower. The mesh is selected in accordance with the trichomes or other plant matter size that is intended to be separated from the other plant matter, which can be larger or smaller depending on the plant species and state of maturity, as well as if the intent is to separate other plant materials, such as pollens or seeds.

In the case of processing the flower and buds that have been trimmed from Cannabis plants, the inert freezing agent is preferably introduced at a quantity, rate and volume sufficient to rapidly reduce the temperature to at least about −60° F. to about −65° F. or lower. When an inert gas such as liquid carbon dioxide is introduced at a temperature of about −100 to −110° F. this temperature drop occurs in about 2-3 minutes. The rapid temperate drop from injecting liquid $CO_2$ rapidly freezes the flowers and bud such that the resin filled trichomes separate from them by breaking free, and also become harder and less sticky as the viscous resins therein solidify. A finer mesh or screen is preferably used in this aspect of the inventive process, such as a screen or mesh with hole sizes in the range of about 25 microns (0.025 mm) to 200 microns (0.2 mm) or 300 microns (0.3 mm), depending on the desired trichome size, which may differ with plant species. This process can be completed in additional 5-15 minutes of turning or rotating the container 311, after the initial 2-3 of turning or rotating the container 311 during the phase of cooling to about −60° F. More specifically it generally requires about 1-3 minutes of additional turning or rotating per lb. of material. The process generates a resin, or at least a resin rich concentrate, commonly known as kief for Cannabis resin extracts. The prior trimming process of the uncured leaves takes only about 30 seconds to a minute of additional turning or rotating per lb. When desired, dry or cured plant matter can also be trimmed or sugar and palm leaves by the first step as described above for green or uncured plant matter. However, if these temperatures cannot be reached due to the chamber size or other restraints, a temperature of about −20° F. can be sufficient, when longer process times are used.

It should be noted that an unexpected result of using an inert or inert liquid freezing agent is the discovery of temperature ranges that can selectively fracture sugar and palm leaves, for removal, without significantly disintegrating the flower and buds, while a lower temperature is effective in disintegrating the flower and buds to the extent necessary to liberate the resin bearing trichomes. This enables full processing of Cannabis and other plant species immediately after harvest when in the uncured state to extract useful materials, such as CDB and THC-A without degradation.

Liquid $CO_2$ can be used or metered from compressed gas tanks with the manually opening of the main gas valve, which is preferably connect to an insulated high pressure rated hose line leading to the chamber 100, and more preferred fed to the chamber via a coupling or portal in the chamber 100, the support frame 200, but preferably directly into the container 311 of the plant matter.

Sufficient freezing rates to reduce the environment of the plant matter to about −60 to −65° F. can be obtained with about 15 lbs of plant matter in a 20 gallon capacity chamber in about 3 minutes from a tank of liquid $CO_2$ compressed to about 800 psi, utilizing about 25 lbs. of the $CO_2$. Such tanks can be used even when the pressure drops to about 250 psi from prior process use. An adequate flow rate of liquid $CO_2$ can be obtained by measuring the tank weight loss, which for the above parameters is about 8 lbs./minute. Alternatively, or additionally the temperature can be monitored inside the chamber. Approximately about 5-8 lbs. of liquid $CO_2$ would be sufficient for "trimming" about 3 lbs. of plant matter in a 5 gallon capacity chamber. Alternatively, about 8-15 lbs. of liquid $CO_2$ can be used for trimming about 5 to 10 lbs. of plant matter in a 20 gallon capacity chamber. Trimming separation vs. the production of trichome resin glands, kief, from the separated flower and bud, requires about 70-75 percent less liquid $CO_2$.

Thus, it is likely that about 1.5 to 4 lbs. of liquid $CO_2$ are required per pound of plant matter. It should be appreciated as a smaller capacity chamber has a larger surface area to volume ratio, the higher consumption of liquid $CO_2$ may be due to heat losses. It is expected that the consumption of the $CO_2$ could be reduced to improve efficiency at lower environmental chamber, but more preferably with thermal insulation of the chamber and/or using larger chambers. Colder inert liquids, such as liquid nitrogen may also require less inert freezing agent relative to the consumption of $CO_2$ reported above. Preferred rates of temperature drop and liquid freezing agent consumption can be readily developed using the above ranges as general guidelines. Liquid nitrogen and liquid $CO_2$ are examples of preferred liquid freezing agents, being compressed gases, they disperse on heating toward room temperature, and readily available. Other compressed gases can be used to provide liquid freezing agents, such as argon, helium, neon and the like. It should be appreciated that if a gasket is used to seal the chamber, it should either be configures to slowly vent the expanding gas, or more preferably a safety pressure release valve should be deployed on the chamber 100.

It has also been discovered that improved efficiency of an inert freezing agent can be obtained when the source container or tank of the material is thermally insulated, such as will blankets, radiation barrier constructions and double wall or vacuum insulation. Hence, the inert freezing agent can be a liquid freezing agent can be supplied from any type of container 1320 (see FIGS. 13C and 13D), such as unpressurized or pressurized cryogenic Dewar type containers (which have vacuum insulation from a double wall construction). A gaseous or liquid inert freezing agent can be applied at varying pressure using any form of regulation, such as pressure regulation. Pressure regulation may also be obtained by letting the liquid freezing agent first expand in an adjacent chamber, so that a cold gaseous form of the agent is released in the chamber at a reduced and regulated pressure. The cold gaseous form of cryogenic liquids can also be released directly from specialized but commercially available containers. As such container 1320 can be configured to release both the gaseous and liquid form of the inert freezing agent, as mixture of the phases can be added to the chamber simultaneously or sequentially via the same of different nozzles, and optionally as a nozzle that produces a jet of liquid, gas or mixture thereof. Liquid freezing agents may be preferred when rapid freezing is desired as they more rapidly transfer heat on direct contact with plant matter.

In another embodiment of the invention, an inert freezing agent may be solid $CO_2$, commonly known as dry ice. However, it is less desirable because it does not provide the rapid chilling that causes fragmentation of the sugar leaves, which enables the novel trimming process discussed above. Dry ice can be also used in the inventive apparatus to the extent one is processing material that is already trimmed, or using trimmed sugar and/or palm or big leaves to further extract the trichome that a represent at a lower density, The various embodiments of the inventive apparatus can be used with dry ice, which for most forms of plant matter in which it is desirable to have cold processing, are preferably in the form of pellets or chips up to about a 0.5 in. in the maximum dimension, as well as with larger circa 0.5 to 2 inch square size cubes or comparable or larger sized balls. Smaller pellets or chips are more effective in chilling material rapidly, such as to solidify and harden viscous or sticky resin components, such as the product of the glandular trichomes which remain attached thereto, while larger ball or cubes are helpful agitating agents. Small pellets and larger cubes or balls of dry ice can be used together. Balls and other agitation means also adding in precluding a gradual build up of the resin on the exterior of the mesh or filter, as more trichome resin particles pass through the holes therein. Having made these discoveries, it will now be appreciated that other agitation means can also accomplish this goal, such as vibration and/or impact with balls or other instruments on the exterior of the filter mesh where the buildup can occur.

Further, any of the above methods of using solid or liquid freezing agents can be used to fracture plant matter and harden trichome resin before adding water and other fluids to enhance the tumbling and mixing of material in the rotating chamber that improves the sieving efficiency.

Figure 12:
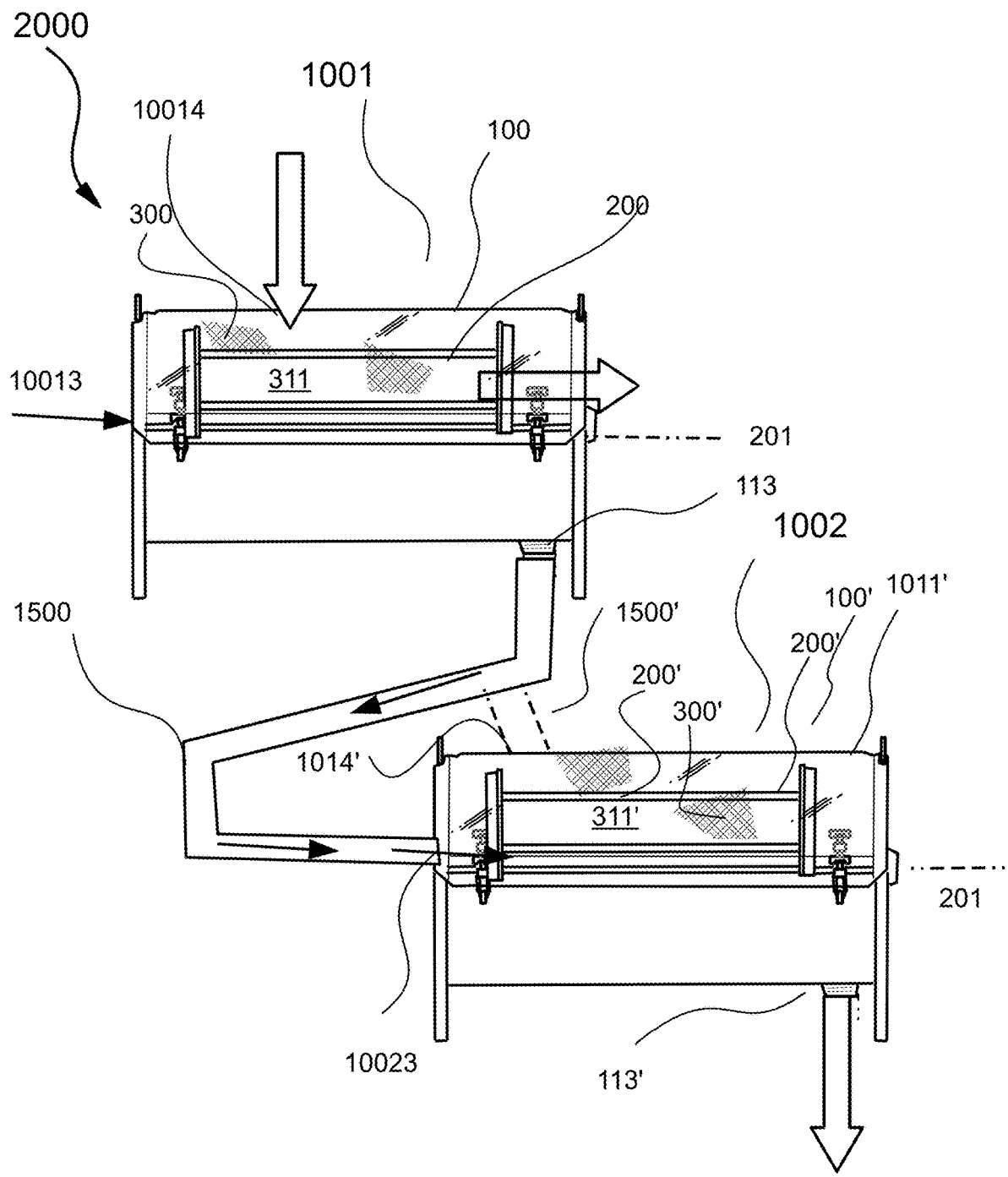
FIG. 12 is a schematic diagram illustrating an alternative embodiment of the invention using 2 or more of the inventive apparatus in a variety of inventive processes or methods.

Another preferred aspect of any of the above processes is process and apparatus illustrated in FIG. 12, in which first and second extractor are connected for use in series. As a non-limiting example of such use, fragmented leaves, bracts and bracteoles, which may be primary sugar leaves of Cannabis, separated in a first rotary extractor 1001 undergoes further processing in a second rotary separator 1002 to extract the trichomes there from. In such an embodiment it is also preferred that the separation method deploy a first and second horizontal axis rotary separation apparatus, each having a chamber 100 or 100' having an inlet port 10013 or 10023 at the side and an outlet or drainage port 113 and 113' at the bottom, a rotating filter support frame 200 adapted to rotate about a cylindrical axis 201 thereof to provide a cylindrical cavity defined by a connected upper and lower cylindrical base, a filter member 300 or 301' adapted to form an enclosed space or container 311 over the filter support frame 200 and 200' a rotary drive means adapted to turn or rotate the rotating filter support frame 200 and 200' about a primary axis 201 thereof that is disposed in a horizontal plane.

The rotary drive means in any embodiment can be a separate motor on each apparatus, or one motor connected by gears, chains, pulleys and/or direct to both chambers, such as but not limited or embodiment in FIG. 1-11.

The outlet port of the first horizontal axis rotary separation apparatus is connect to the inlet port of the second horizontal axis rotary separation apparatus. The inlet port is through a side wall for admitting effluent, namely fracture "trim" into the second enclosed space of the second cylindrical cavity.

In using this configuration of apparatus 2000, a method of plant matter separation may comprise the steps of admitting plant matter to the enclosed space or container 311 of the first horizontal axis rotary separation apparatus, rotating the rotating filter support frame of the first and second horizontal axis rotary separation apparatus and collecting a purified effluent from the outlet 113' at the bottom of the chamber 100' of the second horizontal axis rotary separation apparatus 1002.

In this method and apparatus, the filter member 300 of the first horizontal axis rotary separation apparatus 1001 has a larger opening size than the filter member 300' of the second horizontal axis rotary separation apparatus 1002, such as to enable the release of fractured trim. Water or another fluid is used to flush fragmented matter into the second horizontal axis rotary separation apparatus, via a connecting conduit 1500. The conduit 1500 can connect to the side entry portal 10023 to directly feed material separated in chamber 100 the container 311' of chamber 100'. Alternatively the conduit can be configured as 1500' to add fluid or gas to the cavity 1001' of chamber 100', such as via the lid. Similarly fluid or gas can be added to chamber 100 via portal 10013, directly to container 311, or via an upper portal 10014. Chamber 100' is shown with an optional upper penetration 10014' for the same purpose, as well as to optionally connect conduit 1500'. The filter member 300' of the second horizontal axis rotary separation apparatus may have a circa 25 to 200 micron mesh opening size to retrain the fractured trim, but allow the passage through the mesh of the smaller glandular trichomes that were on the sugar and/or palm leaves (or some small fraction that may have been released from the flowers and bud in the trimming process) and had been released there form by the combination of additional agitation and or fragmentation in the tumbling process such as from inert balls and/or dry ice.

Any combination of dry tumbling, tumbling with mixtures of water or other fluid and agitation balls or dry ice, liquid $CO_2$ or liquid nitrogen can be used in either the first or second chamber, and can be introduced at any inlet port or via the open bag.

The configuration of FIG. 12 can also be used when it is desired to separate plant or other matter into materials of 2 or 3 size ranges, such as when the objective of the separation process is to separate trichomes by size range, or separate trichomes from "trim" or extract additional trichomes from "trim" or larger leaves. The filters 300 and 300' are selected to provide the desired size of the opening in the mesh thereof.

It should also be understood it is not essential to dry the plant matter before the "trimming" process. A potential advantage of not drying or using so called "green", "wet" or uncured plant matter, is that the inventive process avoids the loss of CBD and the decarboxylation of A type THC, which converts it to more psychoactive form; trans-$\Delta^9$THC. Avoiding this decarboxylation results in product that is richer in non-psychoactive cyclic terpenes, such a CBD, which have other medicinal properties being mimetic of endocannabinoids and their activity with cannabinoids receptors.

The use of liquid $CO_2$ in various embodiments of the extraction process yielded unexpected improvements. First, when trimming at the preferred temperatures, the sugar leaves would fragment without damaging the plant buds and flowers. Hence, using mesh screen with opening in the range form about ¼ inch (6 mm) to about ½ inch (12 mm) these plant fragments would exit the container, while the buds and flower that are rich in trichomes would remain in the chamber defined by the mesh screen. While some trichomes are released in the process and separate out of the container 311 with the fragmented leaves, this material can be processed again using smaller mesh screens of about 25 to 200 microns holes to separate out the solid trichome resin glands. As different plants and stages of growth result in different size and shape trichome, the size of the holes in the mesh is selected according the size of the desired product to maximize speed, yet minimize and transfer of undesirable material. It should be understood from the context of these embodiments that a filter member 300 or container 311 may deploy mesh or other types of perforations. Such perforation will be generally referred to in the FIG.'s with reference no. 305'. When the perforations 305' are formed in a rigid container, the connect of the support disks 231 and 232 can be the rigid container itself, and does not require alternative intervening structures.

The liquid $CO_2$ or inert freezing agent process also significantly reduces the process times, compared with a comparable manual dry trimming process, which might run for 2 to 24 hours to achieve the desired separation. With the liquid $CO_2$ or other inert freezing agent process, equivalent yields from the same plant material are achieved in 15 minutes or less. It should be appreciated that while the liquid $CO_2$ or other inert freezing agent process has the greatest advantage in trimming green (uncured) or cured (dry) plant matter, it can be used in any other separation method. For example, the flowers and buds can be further processed in the same type apparatus in a manner that deliberately release trichome resin beads from this material, where the undesired plant material remains in the drum, but the small free glandular trichomes exit the chamber through a screen having a mesh size of about 25 microns to about 200 microns.

The inventive apparatus can also be used to remove the remaining trichomes on the "trim" material produced by manual, that is hand trimming or the inventive liquid freezing agent process. Manual or such processed trimmed leaves, that is sugar and/or the bigger palm leaves of can be reprocessed with the above liquid freezing agent method. Further water, dry ice, tumbling balls can also be used as a medium to release the trichome beads that are resin rich from any type of plant matter.

Another surprising improvement with the inventive apparatus compared with liquid wet sieving with bags is the faster speed of draining water through a fine mesh bag can take 30 minutes to about 12 hours, while in the inventive apparatus the flush an equivalent amount of water in 5 to 10 minutes for an about 6 to ×24 advantage in speed.

Another aspect of the invention is a means for diverting the flow of a liquid freezing agent, such as liquid $CO_2$, as illustrated in FIG. 13A-C. When high pressure fluid or gas is delivered to the chamber via a narrow inlet, nozzle or orifice, it can exit as a jet, meaning a concentrated direct stream of high velocity fluid that is gaseous, liquid or a combination thereof. One such diverter means is a diverter cap 1310 is attached to a collar 1302 that protrudes through the center of the end 131 or 132 as well as the adjacent ends of disks 231 and 232 of the support frame 200. The inlet 1303 also optionally penetrates any portion of a separation apparatus 1000, such as lateral walls as shown in FIG. 14D. While a jet of inert freezing agent, due to the high flow rates, can quickly freeze material in some instances other effects are undesirable, as explained further below.

As the collar 1302 surrounds the gas or liquid inlet 1303, the liquid stream or jet is interrupted by the center wall 1311 of the diverter 1310. The center wall 1311 may be coupled to the lateral side extensions 1312 of the diverter 1310, with the distal ends 1312b of the extensions optionally coupled to the collar 1302 via a connecting pin 1304 that passes through pair of adjacent holes 1310h and 1302h. The pin 1304 has a ring 1306 or other protuberance at opposing in to retain its position joining the diverter cap 1310 to the collar 1302. The diverter cap 1310 can be connected to the collar 1302 or any other part of the container with other structures, such as screw or bayonet type fasters, as well as rivets, snaps, detents and the like. The diverter cap 1310 is preferable readily removable, such as for using the inventive apparatus in other modes, as well as cleaning and replacement.

The diverter cap 1310 causes the jet of inert gas or liquid freezing agent that impinges on the center wall to flow laterally with respect to the initial jet direction, and then exit the region circumscribe by the diverter cap in the gaps 1305 between the lateral side extensions 1312. The diverter cap 1310 may deploy 2, 3, 4 or more lateral side extensions 1312. Arrow 1350 illustrate in FIG. 13A-C the flow paths of the diverted liquid freezing agent as it exit the gaps 1305 and flow along the interior of the container 311 and the support frame 200. In other embodiments double headed arrows are also used to illustrate the expected flow paths of the liquid freezing agent.

The benefits of using the diverter means is greatest when the plant matter is from the species of lupus or cannabis and the residual portion of the flower is primarily calyxes. The plant matter fragmented by the inert or liquid freezing agent may include one or more of fan leaves and sugar leaves. However the plant flower that are primarily calyxes remain intact as the fan leaves and sugar leaves are fragmented. Less of the trichomes are detached from the calyxes and buds in this process, the trichomes that remain on the flowers and bud, are not contaminated by other fragmented material.

It has been observed that absent the use of an inert freezing agent diverter means tips of flowers and the bottoms are knocked off by high pressure impact of the jet, braking the buds and flowers into popcorn size pieces, with diameter of about 3 to 6 mm, some of which can then fall through the ¼ in. (6.1 mm opening) mesh. It should be appreciated that the preferred use of a diverter means for any jet of gaseous and particularly inert liquid freezing agent keeps flowers intact as well as acts as a pressure regulator might in it avoids direct high velocity impact of matter on the flower directly but yet still cause rapid freezing. The inventive forms of the diverter means minimizes also minimizes trichome loss from the larger flowers, which would separate out with the palm and or sugar leaves via a mesh.

While it is preferable to inject gas and liquid freezing agent directly into the support frame via inlet 1303, alternative inlet locations are at the top of the chamber as illustrated in FIG. 13D. Multiple inlet locations are also possible using any combination of the top, bottom and side of a chamber container the plant matter to be separated or otherwise processed with liquid freezing agent. The inventive aspects of the process may be used with various size chambers, as well as the containers for plant material that vibrate, shake, oscillate, or rotate or process about horizontal or vertical axis.

A preferred construction of the diverter cap 1310 is illustrated in FIGS. 14A and 14B. This preferred construction avoids the built up and clogging by solid $CO_2$ at the periphery 1310 p of the diverter cap 1310. The center wall 1311 preferably has a curvilinear shape without an edge or lip at the periphery 1310. Such an edge or lip would be any protuberance that is a deviation of the continuous curvature or shape of the diverter cap 1310 center wall 1310.

The center wall 1311 can also be planar or multifaceted with planar segments, as shown in FIG. 14C-D, but the continuously and more preferably near spherical curvature is presently preferred, as shown in FIGS. 14A and 14B.

Without a diverter means, such as the diverter cap 1310, chamber side of the orifice or nozzle can clog easily depending on the weight and volume of the plant matter load used in the apparatus. In the case of using liquid CO2 a clump of solid plant matter can freeze in front of the nozzle, then with the jet blocked, further cooling would occur at the nozzle solidifying the liquid CO2 and creating dry ice. While a diverter cap 1310 may have holes in the center wall 1310, these tend to clog when liquid $CO_2$ is used as the inert fluid freezing agent.

Figure 15A:
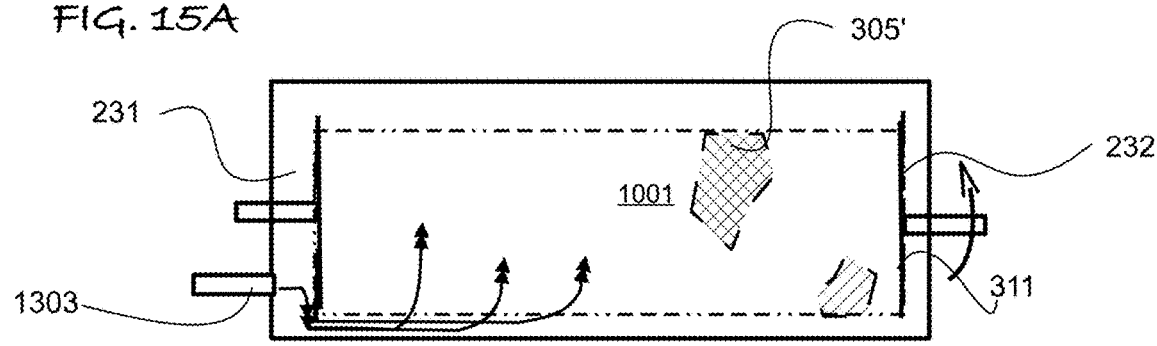
Figure 15B:
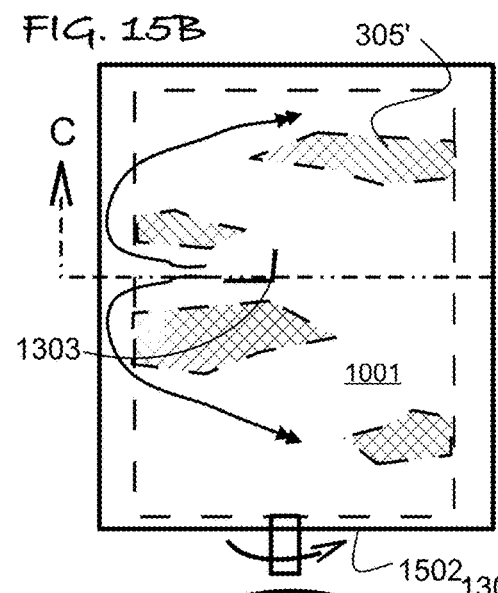
Figure 15D:
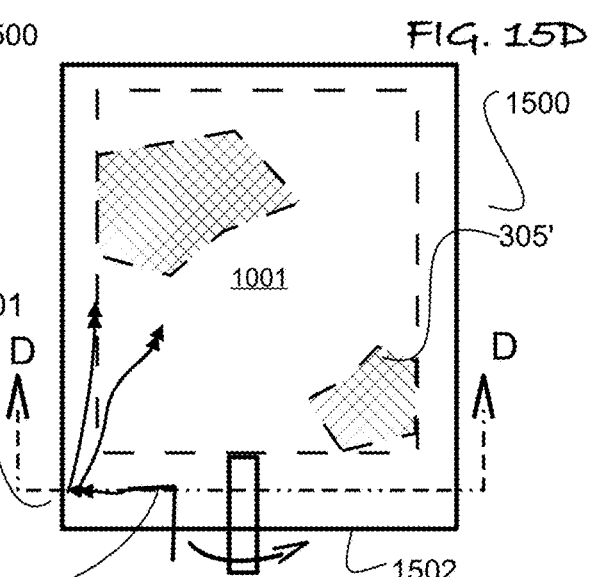
Figure 15C:
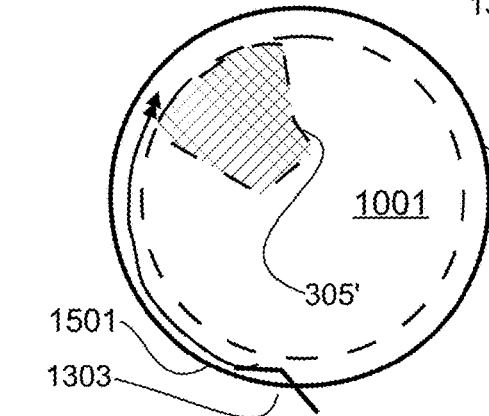
Figure 15E:
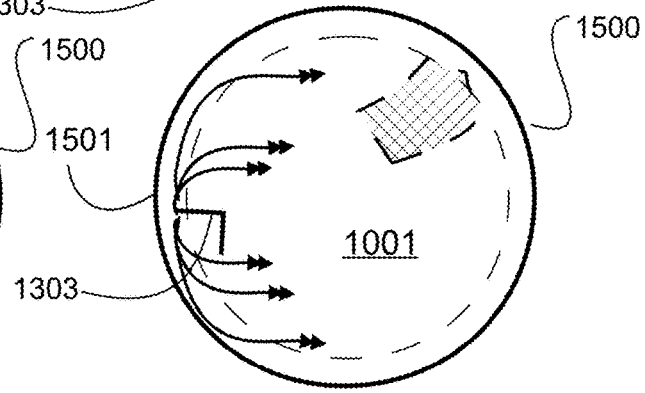

Alternatively, any internal portion of a rotary separation apparatus 1000 can function as a fluid diverter means, when the inlet 1303 is juxtaposed so that the exit orifice thereof directs the jet of inert or liquid freezing agent against it, rather than directly at the plant matter. For example, as shown in FIG. 15A though 15E, both a vertical (FIGS. 15B-E) and horizontal rotary separation apparatus (FIG. 15A) may have a inlet 1302 directed at either on the internal portion of side wall 1501 (FIGS. 15B-E) or a solid part of the filter member 300 as shown in FIG. 15A. In both FIG. 15B-15E a cylindrical chamber 1500 the inlet 1302 can be from the cylindrical side wall 1501 or the circular base 1502, but have the outlet directed to the other wall that is situated generally orthogonal to the principal axis of the inlet tube that forms the direction of the jet of liquid freezing agent. FIG. 15C illustrates another variation in which the liquid jet impinges on internal wall 1501 generally tangential from inlet 1302.

The diverter cap 1210 or equivalent diverting means thereto, improves the separation process in several ways. It avoid the physical deformation of the plant matter caused by the high flow velocity in a direct jet of liquid freezing agent. The desired flowers tend to stay intact, without glandular trichomes into the "trimmed" matter. Also, by using a diverting means the separation of the chlorophyll containing leaves and cellulosic stem materials occur as a fracture process with less shearing and tearing of materials that releases chlorophyll and plant matter lipids. This is a significant advantage over manual or automated "trimming" using blades and related cutting instruments, even when used with considerable care. These and other compounds in leaves and flowers are undesirable. They are difficult to remove from the flower buds and the trichomes in any further process steps, such as solvent or high pressure $CO_2$ extraction methods.

Testing

The attached appendix includes results of analysis of the resulting products from different cannabis strains before and after separation, showing the resulting yields of specific Cannabinoids, the total THC and CBD concentrations, as summarized in the Tables that follows:

| | run | | | |
|---|---|---|---|---|
| Strain | Before total THC | After total THC | Before total CBD | After total CBD |
| Dutch Berry | 18.4 | 19.9 | 0 | 0.3 |
| Dutch Berry | 20.2 | 19.6 | 0 | 0 |
| Dutch Berry | 19.1 | 19.3 | 0.3 | 0.3 |
| | THC + CBD total | THC + CBD total: After | Total Cannabinoids | Total Cannabinoids: After |
| Grape Ape | 22.7% | 24.2% | 25.8 | 27.4 |
| Grape Ape | 20.3% | 20.2% | 23.0% | 22.9% |
| Grape Ape | 20.2% | 21.2% | 22.9% | 24% |
| Grape Ape | 20.1% | 21.4% | 22.9% | 24.2% |

The initial or "Before" condition is without any processing of the indicated strain of Cannabis that was hand trimming by cutting the stem just below the bud, so that sugar leaves are included. The plant material had been dried after harvesting. The Caannabinoids where solvent extracted and analyzed using standard forms of chromatography. The "after" is of equivalent material from the same batch, after "trimming" with $CO_2$ as described above. The leaves removed are added back in so an equivalent mass of material is tested. Any decrease in Cannabinoids would be due to sample size variation or degradation from the $CO_2$ process. As the deviation in small and slightly positive and negative in each test, the change appears to be only from sample size variation. Hence, the $CO_2$ is not acting as a solvent for the Cannabinoids and carrying them out of the chamber with the discharge of the gaseous $CO_2$.

It should be appreciated that the use of a jet or strong flow of a gaseous or liquid freezing agent to agitate, tumble and/or fragment a mixture of plant materials containing extractible substances, such as resin granules like trichomes can be accomplished in configurations in addition to those generally illustrated in FIGS. 13A-C and 15A-E. This merely requires that the plant matter is held, preferably in a confined space, and the jet or strong flow of inert freezing agent either directly or indirectly agitate the plant matter so that is uniformly cooled to the desired temperature. This agitation can be an external agent, such as a motor to drive the rotation or rotary toggling on the containers, as well as agitation of a container, such as by a vibratory support member. The inert or liquid freezing agent may be used to then uniformly freeze water in the plant material to aid in fragmentation, or to rupture plant cells so that water is frozen as ice crystals, which in an environment that remains cold and void of moisture will eventually sublime. Such at least partially dehydrated plant matter can then also be more efficiently extracted with solvent for the chemical compounds in the trichome, such as with solvent extract or pressurized $CO_2$ extraction methods. It is useful that the container have a least a partially perforated outer portion or portions, such as mesh, if it is desirable to remove smaller fragments than the mesh will contain during the freezing process. However, the container need not be perforated if the intent is to subject the entire contents to solvent extraction or pressurized $CO_2$ extraction methods.

FIGS. 16A and 16B illustrate another embodiment of the invention in which plant mixtures within the contained space 1001 is tumbling by rotation of the of support frame 200 and hence filter member 300. The support frame 200 is coupled in rotary engagement to turbine blade assembly 1610. The inlet 1302 for the liquid freezing agent is directed toward blades 1611 of the turbine blade assembly 1611. The turbine blade assembly 1610 may directly drive the support frame 200 or filter member 300 at same rotary speed rate be connected with fixed or variable gears to de-couple the flow rate of the liquid freezing rate from the rotation speed that affects the tumbling of the plan matter. The turbine blade assembly 1610 is preferably in the same container 1600 as the filter member 300 so that the dispersed jet of liquid freezing agent is operative to rapidly freeze the plant matter therein.

In another alternative embodiment illustrated in FIGS. 16C and D, the turbine blade assembly 1610 way be in the filter container 300 and the jet of liquid freezing agent passes through the mesh before impinging on the turbine blades 1311. The turbine blade assembly can be formed as part of the frame 200 that supports a flexible mesh type filter to define a filter container 300, or as part of a perforated rigid container that also provides the function of containing plant matter that is tumbled.

It should be appreciated that the use of a jet of inert or liquid freezing agent can used in other way to agitate a filter container, for example in addition to the previously described support member in the form of a generally cylindrical frame 200 covered by mesh 305, any shape filter container can be vibrated by a jet of liquid freezing agent impacting a solid portion of such a container when supported in a housing by springs or other pliable support, such as hanging from cable and the like. The jet of fluid can be expected to drive such a container in one direction until a restoring force in the springs drives it forward again, or container has moved so the jet no longer impacts a solid portion of the container so strongly.

An advantage of diverting the liquid freezing in the "trimming" process describe above is a purer and more complete extract of plant resins without the carryover of material from the leafy plant cellular matter, such as cellulosic materials from plant fibers and lipids and chlorophyll from plant cell interiors. As these undesirable components are inherently avoided in the more preferred aspects of using the process, the resulting plant resin products are when not purified further as expected to better appeal to consumer by having a better taste and aroma profile, being less harsh to consume by smoking or inhaling vapors or mists produced without burning. Further, they are also expected to be easier to purify to a higher degree in such solvent or high pressure $CO_2$ extraction methods, if further purification is desired.

While the invention has been described in connection with a multiple embodiments, and particularly preferred embodiment, such descriptions are exemplary in nature and may contain inventive components, aspects and methods that can be used in different combinations than these exemplary embodiments. Hence the specific combination odd combinations, aspects and methods are not intended to limit the scope of the invention to the particular form set forth, but on the contrary, it is intended to cover such alternatives, modifications, and equivalents as may be within the spirit and scope of the invention as defined by the appended claims.

We claim:
1. A rotary axis separation apparatus comprising:
   a) a chamber having at least one or more opening for adding and removing materials,
   b) a filter container adapted to rotate about an axis within the chamber,
   c) a container holding an inert freezing agent in fluid communication with the chamber via an inlet wherein the inlet is configured to direct the inert freezing agent into the chamber as a jet that impinges orthogonally on an inner wall of a fluid diverter cap in which the fluid diverter cap has openings on one or more sides of the inner wall to direct the inert freezing agent to flow outward laterally from the diverter cap.

2. The rotary axis separation apparatus of claim 1 wherein the inlet is configured to direct the inert freezing agent as a jet in a direction parallel to the axis of rotation of the filter chamber.

3. The rotary axis separation apparatus of claim 1 wherein the rotary axis separation apparatus is configured to introduce the inert freezing agent directly into the filter container.

4. The rotary axis separation apparatus of claim 1 wherein the rotary axis separation apparatus is configured to introduce the inert freezing agent directly into the filter container and the fluid diverter cap is disposed in the filter container.

5. The rotary axis separation apparatus of claim 1 wherein the fluid diverter cap is an inner wall of the container.

6. The rotary axis separation apparatus of claim 1 wherein the fluid diverter cap is one of an inner and an outer wall of the filter container.

7. The rotary axis separation of claim 1 wherein the inner wall has a continuous curvilinear shape from a center portion to an outer periphery that forms the openings on the one or more sides of the inner wall.

8. A horizontal axis rotary separation apparatus comprising:
   a) a cylindrical chamber having;
      i) a lower half cylindrical basin with an upper rim and having a first and second circular end plates coupled to opposing end of lower half cylindrical basin that extend above the upper rim,
      ii) an upper half cylindrical lid with a lower rim, adapted for connecting to the upper rim and an upper periphery of the first and second circular end plates that extends above the upper rim,
   b) a rotating filter support frame adapted to rotate about a cylindrical axis thereof to provide a cylindrical cavity defined by a connected upper and lower cylindrical base,
   c) a removable filter member adapted to form an enclosed space over the filter support frame,
   d) a rotary drive means adapted to rotate the opposing ends of the rotary support frame in the first and second circular end plates, and
   e) a rotary drive coupling to support opposing ends of the rotary support frame in the first and second circular end plates.

9. The horizontal axis rotary separation apparatus of claim 8 wherein the upper half of the cylindrical lid is coupled to the lower half cylindrical base by one or more hinges disposed at an adjacent portion of the upper and lower rims thereof, the hinge being disposed for adjacent placement of the upper half to the lower half.

10. The horizontal axis rotary separation apparatus of claim 8 wherein the removable filter member has longitudinal side zipper that extends substantially between the upper and lower cylindrical base.

11. The horizontal axis rotary separation apparatus of claim 8 wherein the removable filter member has a circumferential reinforcement band disposed between opposing ends.

12. A rotary axis separation apparatus comprising:
   a) a chamber having at least one or more openings for adding and removing materials,
   b) a filter container adapted to rotate about an axis within the chamber,
   c) a containing holding an inert freezing agent in fluid communication with the chamber
   wherein the chamber has a first portal for introducing material to be separated into the filter container and a second portal for introducing the inert freezing agent into the chamber,
   wherein the chamber comprises:
   d) a cylindrical chamber having;
      i) a lower half cylindrical basin with an upper rim and having a first and second circular end plates coupled to opposing end of lower half cylindrical basin that extend above the upper rim,
      ii) an upper half cylindrical lid with a lower rim, adapted for connecting to the upper rim and an upper periphery of the first and second circular end plates that extends above the upper rim,
   e) a rotating filter support frame adapted to rotate about a cylindrical axis thereof to provide a cylindrical cavity defined by a connected upper and lower cylindrical base,
   f) a removable filter member adapted to form an enclosed space over the filter support frame,
   g) a rotary drive means adapted to rotate the opposing ends of the rotary support frame in the first and second circular end plates, and
   h) a rotary drive coupling to support opposing ends of the rotary support frame in the first and second circular end plates.

13. The rotary axis separation apparatus according to claim 12 further comprising a fluid diverter means disposed in front of the second portal for introducing the inert freezing agent into the chamber.

14. The rotary axis separation apparatus of claim 13 wherein the second portal is configured to introduce the inert freezing agent directly into the filter container and the fluid diverter means is disposed in the filter container.

15. A rotary axis separation apparatus comprising:
   a) a chamber having at least one or more openings for adding and removing materials,
   b) a filter container adapted to rotate about an axis within the chamber,
   c) a mesh filter formed of a rectangular expanse of a material that covers the filter container,
   d) a means for introducing an inert freezing agent into the chamber.

16. The rotary axis separation apparatus according to claim 15 wherein the mesh has openings with a size from 0.25 inches to 0.5 inches.

17. The rotary axis separation apparatus according to claim 15 wherein the filter container comprises;
   a) two spaced apart support disks to define the bases of a cylinder that includes a cylindrical axis,
   b) at least one coupling rod extending between the spaced apart support disks that is disposed parallel to the axis of the cylinder.

18. The rotary axis separation apparatus according to claim 17 wherein the mesh filter is formed of a rectangular expanse of a material having a first pair of opposing sides that extends around a perimeter of each spaced apart support disk to generally define a surface of the cylinder.

19. The rotary separation apparatus according to claim 17 wherein at least one of the spaced apart support disks have an annular flange that extends about a perimeter of the support disk to form an adjacent portion of a surface of the cylinder.

20. The rotary separation apparatus according to claim 19 wherein at least one side of the mesh filter extends over the annular flange of the support disk.

21. The rotary separation apparatus according to claim 19 wherein the at least one side of the mesh filter that extends over the annular flange of the support disk is attached to the annular flange with hook and loop fasteners.

22. The rotary separation apparatus according to claim 21 wherein the second pair of opposing sides are removably connected on the surface of the filter container by a connecting zipper.

23. The rotary axis separation apparatus according to claim 15 wherein the mesh filter has at least one flap like opening that provides for a first region of a surface of the filter container to be folded way from a surface of the filter container to form an opening for adding and removing materials to and from the filter container.

24. The rotary separation apparatus according to claim 23 wherein the at least one flap like opening on the mesh filter has a zippered connection to an adjacent part of the mesh filter by an access zipper.

25. The rotary separation apparatus according to claim 15 wherein the rectangular expanse of a material that forms the mesh filter has a second pair of opposing sides disposed orthogonal to the first pair of opposing sides in which the second pair of opposing sides are removably connected on a surface of the filter container.

26. The rotary separation apparatus according to claim 15 further comprising an enclosure configured to cover the filter container and retain material that passes through the mesh filter when the filter container is rotated.

27. The rotary separation apparatus according to claim 26 wherein the enclosure is configured to direct material that passes through the mesh filter when the cylinder is rotated to an exit portal.

28. The rotary separation apparatus according to claim 15 wherein the means for introducing an inert freezing agent into the chamber is a container holding an inert freezing agent in fluid communication with the chamber and the inert freezing agent in the container is one of carbon dioxide and liquid nitrogen.

\* \* \* \* \*